US 10,164,196 B2

United States Patent
Nakaie et al.

(10) Patent No.: US 10,164,196 B2
(45) Date of Patent: Dec. 25, 2018

(54) ANILINE DERIVATIVE, CHARGE-TRANSPORTING VARNISH AND ORGANIC ELECTROLUMINESCENT DEVICE

(71) Applicant: NISSAN CHEMICAL INDUSTRIES, LTD., Tokyo (JP)

(72) Inventors: Naoki Nakaie, Funabashi (JP); Taichi Nakazawa, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 247 days.

(21) Appl. No.: 14/899,854

(22) PCT Filed: Jun. 17, 2014

(86) PCT No.: PCT/JP2014/065999
§ 371 (c)(1),
(2) Date: Dec. 18, 2015

(87) PCT Pub. No.: WO2014/203882
PCT Pub. Date: Dec. 24, 2014

(65) Prior Publication Data
US 2016/0141507 A1 May 19, 2016

(30) Foreign Application Priority Data
Jun. 21, 2013 (JP) .................. 2013-130620

(51) Int. Cl.
*C07C 211/54* (2006.01)
*H01L 51/00* (2006.01)
(Continued)

(52) U.S. Cl.
CPC ........ *H01L 51/0059* (2013.01); *C07C 211/54* (2013.01); *C07C 211/58* (2013.01);
(Continued)

(58) Field of Classification Search
CPC ............. H01L 51/0059; H01L 51/5056; H01L 51/5088; C07C 211/54; C07C 211/58;
(Continued)

(56) References Cited

U.S. PATENT DOCUMENTS 6,336,739 B1 * 1/2002 Lee .................. B01F 1/0011
366/143
7,862,747 B2 1/2011 Yoshimoto et al.
(Continued)

FOREIGN PATENT DOCUMENTS

JP 2005-276832 A 10/2005
WO WO 2006/025342 A1 3/2006
(Continued)

OTHER PUBLICATIONS

International Search Report, issued in PCT/JP2014/065999, dated Jul. 29, 2014.
(Continued)

*Primary Examiner* — Harold Y Pyon
*Assistant Examiner* — Danny N Kang
(74) *Attorney, Agent, or Firm* — Birch, Stewart, Kolasch & Birch, LLP

(57) ABSTRACT

Provided is an aniline derivative represented by formula (1).

(In formula (1), $R^1$ represents an alkyl group, an alkenyl group, an alkynyl group, an aryl group having 6-20 carbon atoms, a heteroaryl group, or a group represented by formula (2), and $R^2$-$R^{55}$ independently represent a hydrogen atom, a halogen atom, a nitro group, a cyano group, an aldehyde group, a hydroxy group, a thiol group, a carboxylic acid group, an alkyl group, an alkenyl group, an alkynyl group, an aryl group, a heteroaryl group, etc.)

13 Claims, No Drawings

(51) Int. Cl.
*C07C 211/61* (2006.01)
*C07C 211/58* (2006.01)
*H01L 51/50* (2006.01)

(52) U.S. Cl.
CPC ........ C07C 211/61 (2013.01); *C07C 2603/24* (2017.05); *C07C 2603/26* (2017.05); *H01L 51/5056* (2013.01); *H01L 51/5088* (2013.01)

(58) Field of Classification Search
CPC ............... C07C 211/61; C07C 2603/24; C07C 2603/26
USPC ........................................................ 252/500
See application file for complete search history.

(56) References Cited

U.S. PATENT DOCUMENTS

| | | |
|---|---|---|
| 8,298,444 B2 | 10/2012 | Yamada et al. |
| 8,906,519 B2 | 12/2014 | Kato et al. |
| 2005/0208334 A1 | 9/2005 | Lee et al. |

FOREIGN PATENT DOCUMENTS

| | | | | |
|---|---|---|---|---|
| WO | WO 2007/079103 A2 | 7/2007 | | |
| WO | WO 2008/032616 A1 | 3/2008 | | |
| WO | WO 2008/129947 A1 | 10/2008 | | |
| WO | WO 2010/058777 A1 | 5/2010 | | |
| WO | WO 2010058777 A1 * | 5/2010 | ......... | H01L 51/0035 |

OTHER PUBLICATIONS

Written Opinion of the International Searching Authority, issued in PCT/JP2014/065999, dated Jul. 29, 2014.

* cited by examiner

ANILINE DERIVATIVE, CHARGE-TRANSPORTING VARNISH AND ORGANIC ELECTROLUMINESCENT DEVICE

TECHNICAL FIELD

This invention relates to an aniline derivative, a charge-transporting varnish, and an organic electroluminescent (organic EL) device.

BACKGROUND ART

Charge-transporting thin-films made of organic compounds are used as emissive layers and charge injection layers in organic EL devices. In particular, a hole injection layer is responsible for transferring charge between an anode and a hole transport layer or an emissive layer, and thus serves an important function in achieving low-voltage driving and high brightness in organic EL devices.

Processes for forming the hole injection layer are broadly divided into dry processes such as vapor deposition and wet processes such as spin coating. Comparing these different processes, wet processes are more capable of efficiently producing thin-films having a high flatness over a large surface area. Hence, with the progress currently underway toward organic EL displays of larger surface area, there exists a desire for hole injection layers that can be formed by wet processes.

In view of these circumstances, the inventors have developed charge-transporting materials which can be employed in various wet processes and which, when used in hole injection layers for organic EL devices, are capable of achieving excellent EL device characteristics. The inventors have also developed compounds of good solubility in organic solvents for use in such charge-transporting materials (see, for example, Patent Documents 1 to 4).

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777

SUMMARY OF THE INVENTION

Problems to be Solved by the Invention

It is therefore an object of this invention to provide a novel aniline derivative which, as with the prior art in the above patent publications, exhibits good solubility in organic solvents and, when formed into a thin-film and used as a hole injection layer, enables an organic EL device endowed with excellent electrical characteristics to be achieved. Further objects of the invention are to provide a charge-transporting varnish containing such an aniline derivative, and an organic EL device.

Means for Solving the Problems

The inventors have conducted extensive investigations, as a result of which they have discovered that specific aniline derivatives exhibit a high solubility in organic solvents. They have also found that thin-films obtained from varnishes prepared by dissolving such an aniline derivative together with a dopant in an organic solvent have high charge-transporting properties, and that such thin-films, when used as a hole injection layer in an organic EL device, are capable of achieving excellent electrical characteristics.

Accordingly, the invention provides the following aniline derivatives, charge-transporting varnishes and organic EL devices.

1. An aniline derivative characterized by having formula (1)

[Chemical Formula 1]

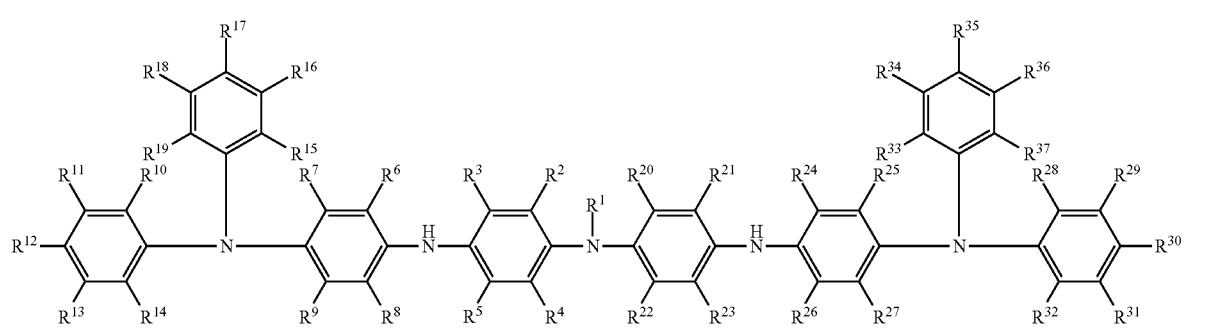

(1)

(wherein $R^1$ is an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, a heteroaryl group of 2 to 20 carbon atoms which may be substituted with $Z^2$, or a group of formula (2)

[Chemical Formula 2]

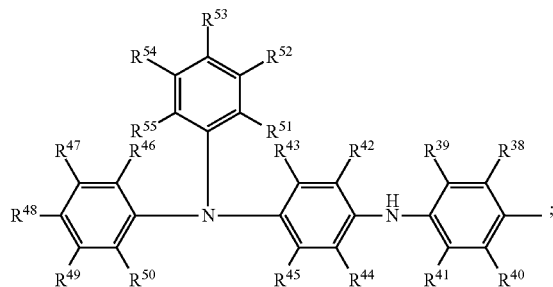

(2)

$R^2$ to $R^{55}$ are each independently a hydrogen atom, a halogen atom, a nitro group, a cyano group, an aldehyde group, a hydroxyl group, a thiol group, a carboxyl group, an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, a heteroaryl group of 2 to 20 carbon atoms which may be substituted with $Z^2$, —C(O)Y$^1$, —OY$^2$, —SY$^3$, —C(O)OY$^4$, —OC(O)Y$^5$, —C(O)NHY$^6$ or —C(O)NY$^7$Y$^8$;

$Y^1$ to $Y^8$ are each independently an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, or a heteroaryl group of 2 to 20 carbon atoms which may be substituted with $Z^2$;

$Z^1$ is a halogen atom, a nitro group, a cyano group, an aldehyde group, a hydroxyl group, a thiol group, a sulfonic acid group, a carboxyl group, an aryl group of 6 to 20 carbon atoms which may be substituted with $Z^3$, or a heteroaryl group of 2 to 20 carbon atoms which may be substituted with $Z^3$;

$Z^2$ is a halogen atom, a nitro group, a cyano group, an aldehyde group, a hydroxyl group, a thiol group, a sulfonic acid group, a carboxyl group, an alkyl group of 1 to 20 carbon atoms which may be substituted with $Z^3$, an alkenyl group of 2 to 20 carbon atoms which may be substituted with $Z^3$, or an alkynyl group of 2 to 20 carbon atoms which may be substituted with $Z^3$; and $Z^3$ is a halogen atom, a nitro group, a cyano group, an aldehyde group, a hydroxyl group, a thiol group, a sulfonic acid group or a carboxyl group).

2. The aniline derivative of 1 above, wherein $R^2$ to $R^{37}$ are a hydrogen atom, a halogen atom, an alkyl group of 1 to 20 carbon atoms which may be substituted with $Z^1$, an aryl group of 6 to 20 carbon atoms which may be substituted with $Z^2$, or —OY$^2$.

3. The aniline derivative of 1 or 2 above, wherein $R^1$ is an alkyl group of 1 to 20 carbon atoms which may be substituted with $Z^1$, an aryl group of 6 to 20 carbon atoms which may be substituted with $Z^2$, or a group of formula (2).

4. The aniline derivative of 3 above, wherein $R^1$ is a group of formula (2).

5. The aniline derivative of 4 above, wherein $R^{38}$ to $R^{55}$ are a hydrogen atom, a halogen atom, an alkyl group of 1 to 20 carbon atoms which may be substituted with $Z^1$, an aryl group of 6 to 20 carbon atoms which may be substituted with $Z^2$, or —OY$^2$.

6. A charge-transporting substance consisting of the aniline derivative of any one of 1 to 5 above.

7. A charge-transporting varnish which includes the aniline derivative of any one of 1 to 5 above, a dopant and an organic solvent.

8. A charge-transporting thin-film produced using the charge-transporting varnish of 7 above.

9. A charge-transporting thin-film which includes the aniline derivative of any one of 1 to 5 above.

10. An electronic device which includes at least one charge-transporting thin-film of 8 or 9 above.

11. An organic electroluminescent device which includes at least one charge-transporting thin-film of 8 or 9 above.

12. The organic electroluminescent device of 11 above, wherein the charge-transporting thin-film is a hole injection layer or a hole transport layer.

13. A method of preparing the aniline derivative of 1 above, which method includes the step of reacting an amine compound of formula (3), an amine compound of formula (4) and an amine compound of formula (5) in the presence of a catalyst

[Chemical Formula 3]

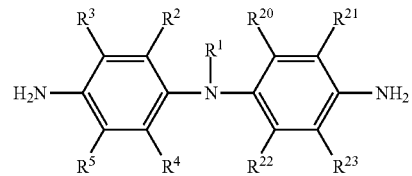

(3)

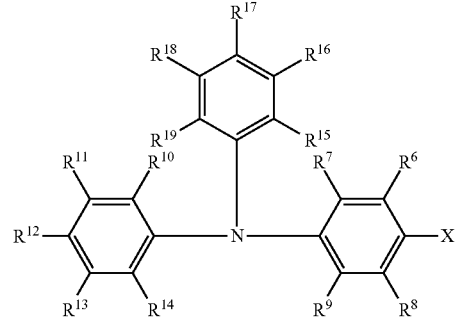

(4)

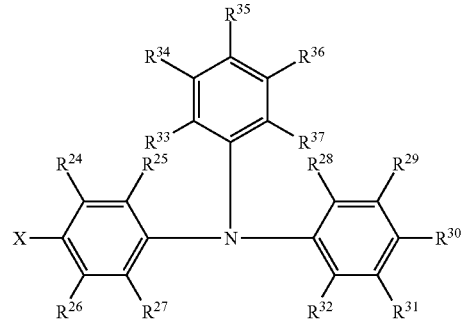

(5)

(wherein $R^1$ to $R^{37}$ are as defined above, and X is a halogen atom or a pseudo-halogen group).

14. A method of preparing the aniline derivative of 1 above, which method includes the step of reacting an amine compound of formula (6), an amine compound of formula (7) and an amine compound of formula (8) in the presence of a catalyst

[Chemical Formula 4]

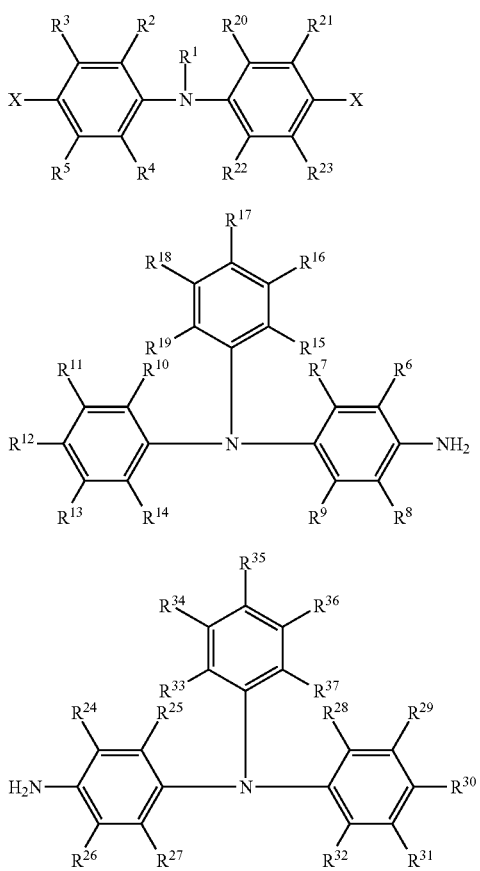

(wherein $R^1$ to $R^{37}$ are as defined above, and X is a halogen atom or a pseudo-halogen group).

15. A method of preparing the aniline derivative of 4 above, which method includes the step of reacting an amine compound of formula (9), an amine compound of formula (4), an amine compound of formula (5) and an amine compound of formula (10) in the presence of a catalyst

[Chemical Formula 5]

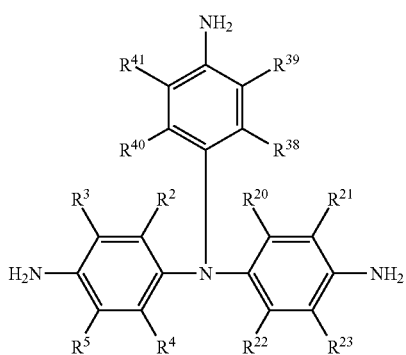

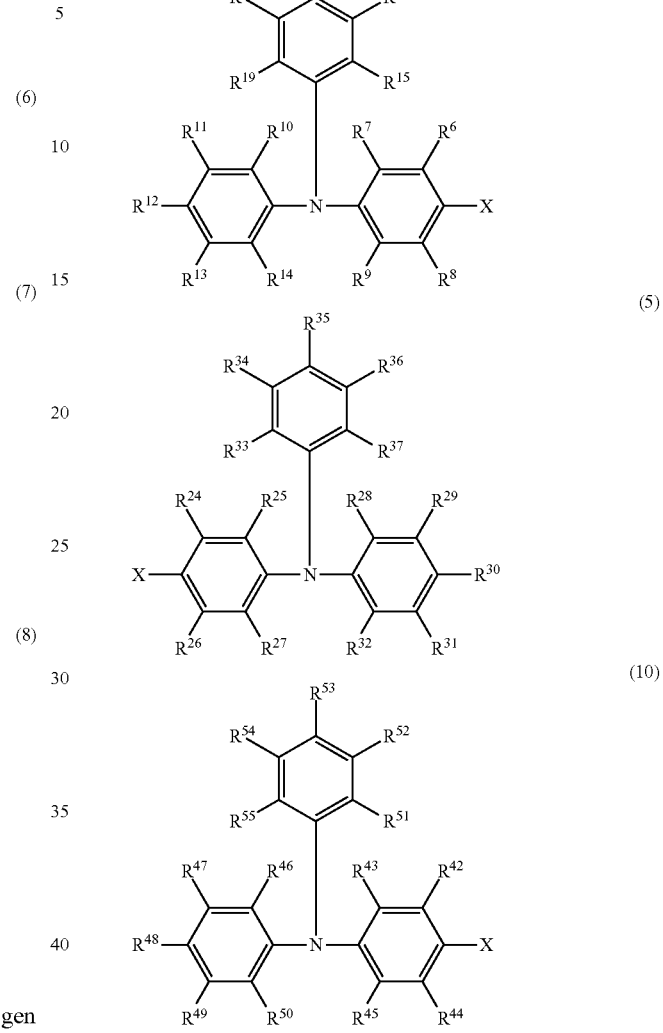

(wherein $R^1$ to $R^{55}$ are as defined above, and X is a halogen atom or a pseudo-halogen group).

Advantageous Effects of the Invention

The aniline derivative of the invention is readily soluble in organic solvents. A charge-transporting varnish can easily be prepared by dissolving the aniline derivative together with a dopant in an organic solvent.

Thin-films produced from the charge-transporting varnish of the invention exhibit high charge-transporting properties, and can thus be advantageously used as thin-films for organic EL devices and other electronic devices. In particular, by employing such a thin-film as a hole injection layer in an organic EL device, an organic EL device having excellent electrical characteristics can be obtained.

Also, the charge-transporting varnish of the invention can reproducibly produce thin-films of excellent charge transportability even using various wet processes capable of film formation over a large surface area, such as spin coating or slit coating, and is thus capable of fully accommodating recent advances in the field of organic EL devices.

EMBODIMENT FOR CARRYING OUT THE INVENTION

[Aniline Derivative]

The aniline derivative according to this invention has formula (1).

[Chemical Formula 6]

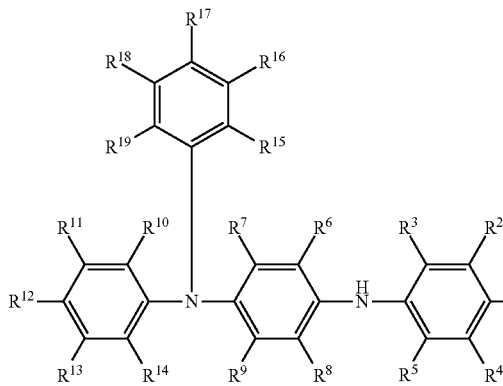
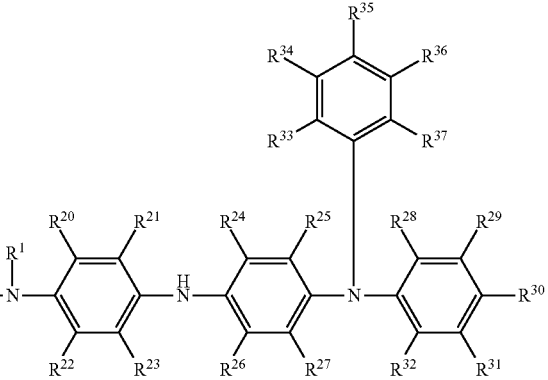

(1)

In the formula, $R^1$ is an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, a heteroaryl group of 2 to 20 carbon atoms which may be substituted with $Z^2$, or a group of formula (2).

[Chemical Formula 7]

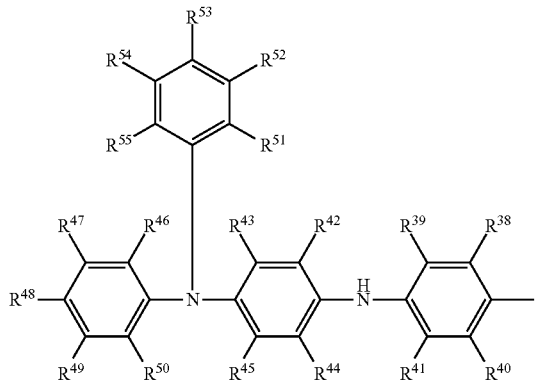

(2)

$R^2$ to $R^{55}$ are each independently a hydrogen atom, a halogen atom, a nitro group, a cyano group, an aldehyde group, a hydroxyl group, a thiol group, a carboxyl group, an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, a heteroaryl group of 2 to 20 carbon atoms which may be substituted with $Z^2$, —C(O)$Y^1$, —O$Y^2$, —S$Y^3$, —C(O)O$Y^4$, —OC(O)$Y^5$, —C(O)NH$Y^6$ or —C(O)N$Y^7Y^8$.

$Y^1$ to $Y^8$ are each independently an alkyl group of 1 to 20 carbon atoms which may be substituted with $Z^1$, an alkenyl group of 2 to 20 carbon atoms which may be substituted with $Z^1$, an alkynyl group of 2 to 20 carbon atoms which may be substituted with $Z^1$, an aryl group of 6 to 20 carbon atoms which may be substituted with $Z^2$, or a heteroaryl group of 2 to 20 carbon atoms which may be substituted with $Z^2$.

$Z^1$ is a halogen atom, a nitro group, a cyano group, an aldehyde group, a hydroxyl group, a thiol group, a sulfonic acid group, a carboxyl group, an aryl group of 6 to 20 carbon atoms which may be substituted with $Z^3$, or a heteroaryl group of 2 to 20 carbon atoms which may be substituted with $Z^3$.

$Z^2$ is a halogen atom, a nitro group, a cyano group, an aldehyde group, a hydroxyl group, a thiol group, a sulfonic acid group, a carboxyl group, an alkyl group of 1 to 20 carbon atoms which may be substituted with $Z^3$, an alkenyl group of 2 to 20 carbon atoms which may be substituted with $Z^3$, or an alkynyl group of 2 to 20 carbon atoms which may be substituted with $Z^3$.

$Z^3$ is a halogen atom, a nitro group, a cyano group, an aldehyde group, a hydroxyl group, a thiol group, a sulfonic acid group or a carboxyl group.

Specific examples of halogen atoms include fluorine, chlorine, bromine and iodine atoms.

The alkyl group of 1 to 20 carbon atoms may be linear, branched or cyclic. Specific examples of such alkyl groups include linear or branched, acyclic alkyl groups of 1 to 20 carbon atoms such as methyl, ethyl, n-propyl, isopropyl, n-butyl, isobutyl, s-butyl, t-butyl, n-pentyl, n-hexyl, n-heptyl, n-octyl, n-nonyl and n-decyl; and cyclic alkyl groups of 3 to 20 carbon atoms such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl and bicyclodecyl groups.

The alkenyl group of 2 to 20 carbon atoms may be linear, branched or cyclic. Specific examples of such alkenyl groups include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pententyl, n-1-decenyl and n-1-eicosenyl groups.

The alkynyl group of 2 to 20 carbon atoms may be linear, branched or cyclic. Specific examples of such alkynyl groups include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

The number of carbon atoms on the alkyl, alkenyl and alkynyl groups is preferably 12 or less, more preferably 6 or less, and even more preferably 4 or less.

Specific examples of aryl groups of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups.

Specific examples of heteroaryl groups of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

The number of carbon atoms on the aryl and heteroaryl groups is preferably 14 or less, more preferably 10 or less, and even more preferably 6 or less.

$R^1$ is preferably an alkyl group of 1 to 20 carbon atoms which may be substituted with $Z^1$, an aryl group of 6 to 20 carbon atoms which may be substituted with $Z^2$, or a group of formula (2); more preferably an alkyl group of 1 to 10 carbon atoms which may be substituted with $Z^1$, a phenyl group which may be substituted with $Z^2$, or a group of formula (2); and most preferably a group of formula (2).

When $R^1$ is a group of formula (2), $R^{38}$ to $R^{55}$ are each independently preferably a hydrogen atom, a halogen atom, an alkyl group of 1 to 20 carbon atoms which may be substituted with $Z^1$, an aryl group of 6 to 20 carbon atoms which may be substituted with $Z^2$, an alkoxy group of 1 to 20 carbon atoms which may be substituted with $Z^1$ (an —$OY^2$ group in which $Y^2$ is an alkyl group of 1 to 20 carbon atoms which may be substituted with $Z^1$), or an aryloxy group of 6 to 20 carbon atoms which may be substituted with $Z^2$ (an —$OY^2$ group in which $Y^2$ is an aryl group of 6 to 20 carbon atoms which may be substituted with $Z^2$); more preferably a hydrogen atom, a fluorine atom, an alkyl group of 1 to 10 carbon atoms which may be substituted with $Z^1$, or a phenyl group which may be substituted with $Z^2$; even more preferably a hydrogen atom, a fluorine atom, or a phenyl group which may be substituted with $Z^2$; and most preferably a hydrogen atom.

$R^2$ to $R^{37}$ are each independently preferably a hydrogen atom, a halogen atom, an alkyl group of 1 to 20 carbon atoms which may be substituted with $Z^1$, an aryl group of 6 to 20 carbon atoms which may be substituted with $Z^2$, an alkoxy group of 1 to 20 carbon atoms which may be substituted with $Z^1$, or an aryloxy group of 6 to 20 carbon atoms which may be substituted with $Z^2$; more preferably a hydrogen atom, a fluorine atom, an alkyl group of 1 to 10 carbon atoms which may be substituted with $Z^1$, or a phenyl group which may be substituted with $Z^2$; even more preferably a hydrogen atom, a fluorine atom, or a phenyl group which may be substituted with $Z^2$; and most preferably a hydrogen atom.

When $R^2$ to $R^{55}$ and $Y^1$ to $Y^8$ are alkyl groups, alkenyl groups, alkynyl groups, aryl groups or heteroaryl groups, the substituent $Z^1$ is preferably a halogen atom or an aryl group of 6 to 20 carbon atoms which may be substituted with $Z^3$; more preferably a halogen atom or a phenyl group which may be substituted with $Z^3$; and most preferably does not exist (i.e., is non-substituting).

The substituent $Z^2$ is preferably a halogen atom or an alkyl group of 1 to 20 carbon atoms which may be substituted with $Z^3$; more preferably a halogen atom or an alkyl group of 1 to 4 carbon atoms which may be substituted with $Z^3$; and most preferably does not exist (i.e., is non-substituting).

$Z^3$ is preferably a halogen atom, more preferably a fluorine atom, and most preferably does not exist (i.e., is non-substituting).

Specific examples of the aniline derivative of formula (1) include, but are not limited to, those shown below. In the following formulas, "Me" represents a methyl group, "Et" represents an ethyl group, "n-Pr" represents an n-propyl group, "i-Pr" represents an i-propyl group, "n-Bu" represents an n-butyl group, "i-Bu" represents an isobutyl group, "s-Bu" represents an s-butyl group, "t-Bu" represents a t-butyl group, "n-Pen" represents an n-pentyl group, "n-Hex" represents an n-hexyl group, "n-Hep" represents an n-heptyl group, and "Ph" represents a phenyl group.

[Chemical Formula 8]

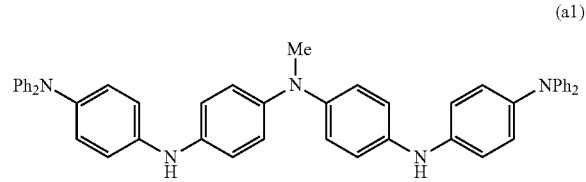
(a1)

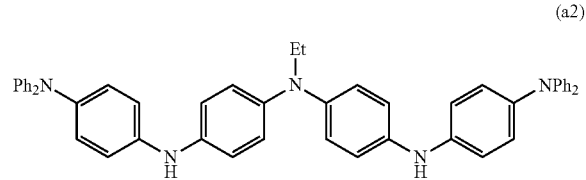
(a2)

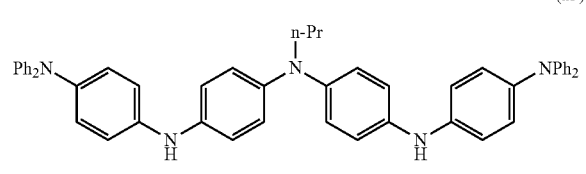
(a3)

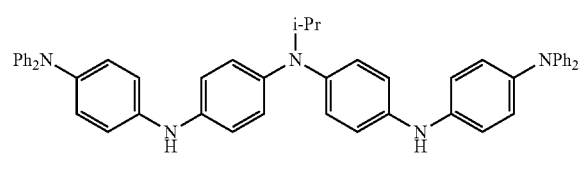
(a4)

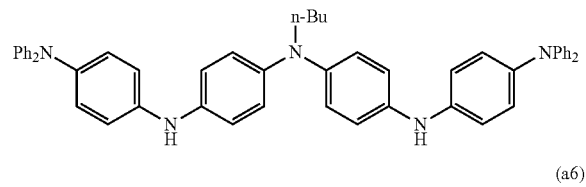
(a5)

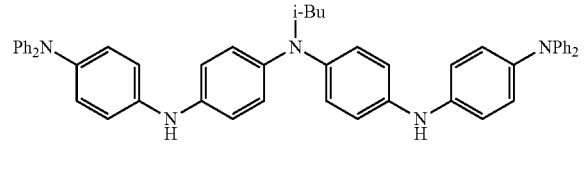
(a6)

(a7) 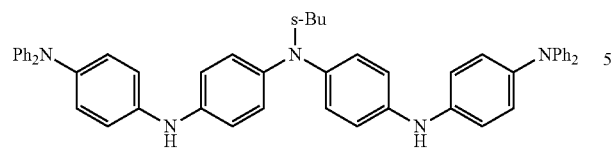
(a8) 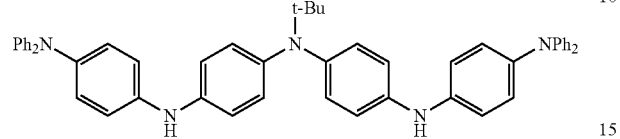
(a9) 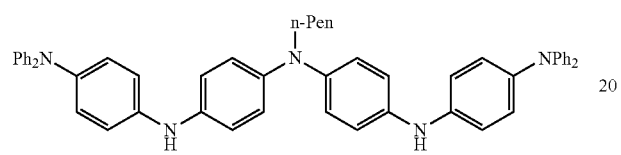
(a10) 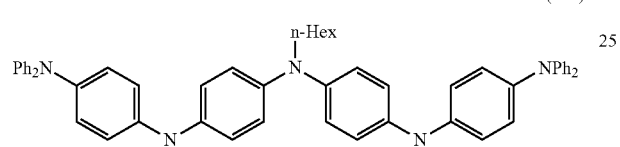
(a11) 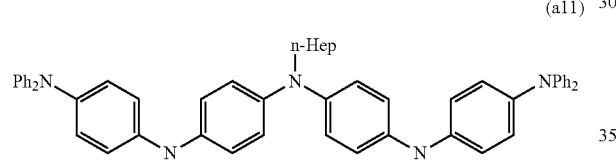
[Chemical Formula 9]
(a12) 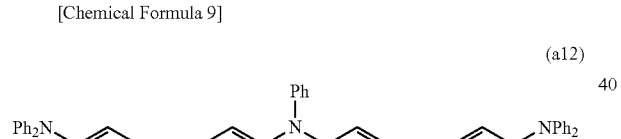
(a13) 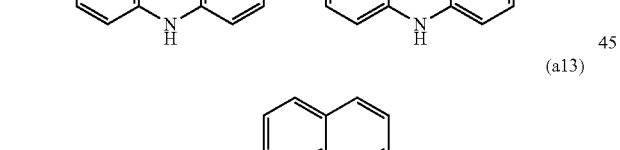
(a14) 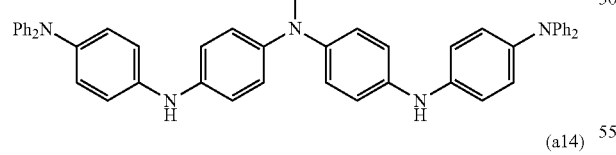
(a15) 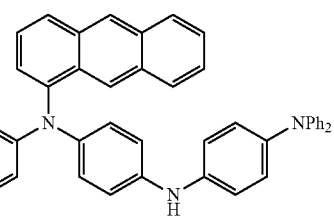
(a16) 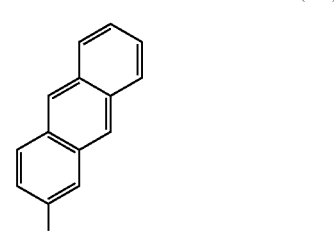
(a17) 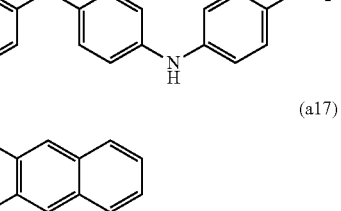
(a18) 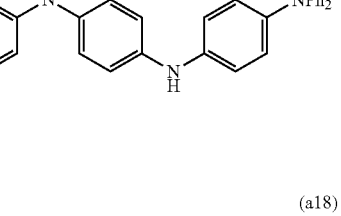
(a19) 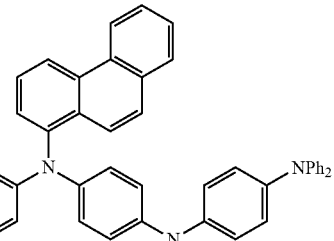

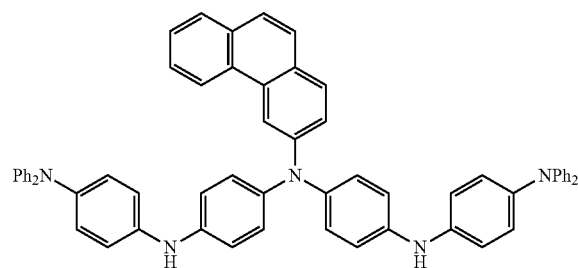
(a20)
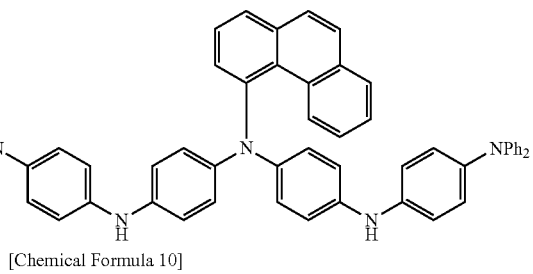
(a22)
[Chemical Formula 10]
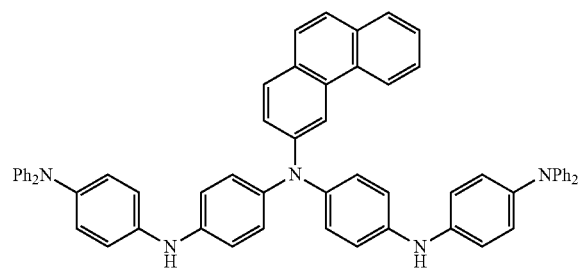
(a21)
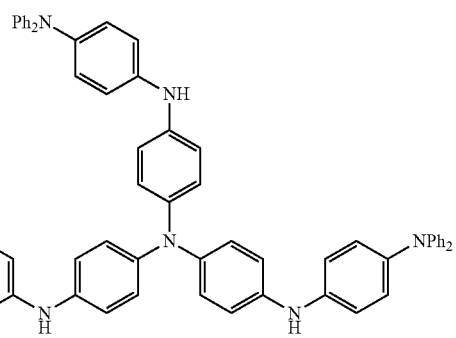
(a23)
[Method of Preparing Aniline Derivative]
The aniline derivative of the invention may be prepared by reacting an amine compound of formula (3), an amine compound of formula (4) and an amine compound of formula (5) in the presence of a catalyst (Scheme 1)
Scheme 1
[Chemical Formula 11]
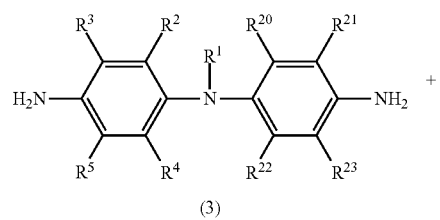
(3)
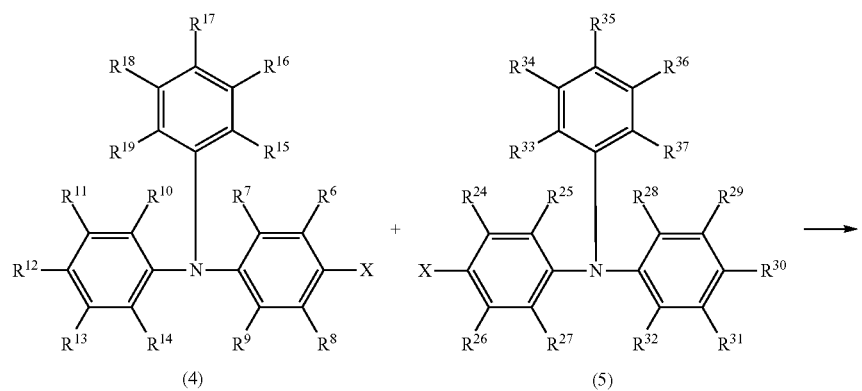

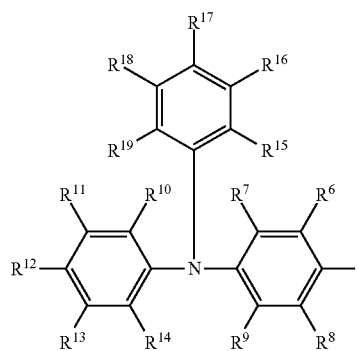

(1)

(wherein each X is independently a halogen atom or a pseudo-halogen group, and $R^1$ to $R^{37}$ are as defined above).

Alternatively, the aniline derivative of the invention may be prepared by reacting an amine compound of formula (6), an amine compound of formula (7) and an amine compound of formula (8) in the presence of a catalyst (Scheme 2)

Scheme 2

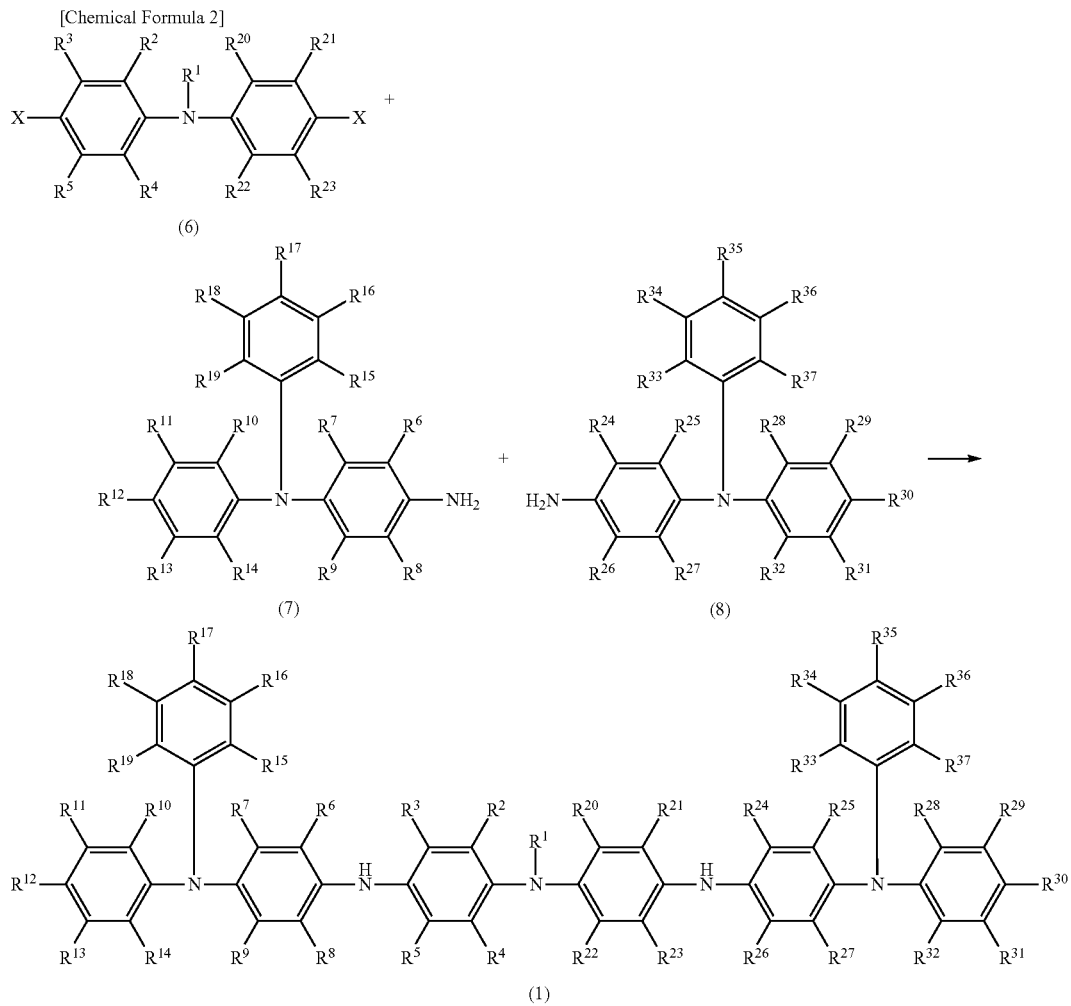

(wherein X and $R^1$ to $R^{37}$ are as defined above).

When $R^1$ is a group of formula (2), the aniline derivative of the invention (formula (1')) may be prepared by reacting an amine compound of formula (9), an amine compound of formula (4), an amine compound of formula (5) and an amine compound of formula (10) in the presence of a catalyst (Scheme 3)
Scheme 3
[Chemical Formula 13]
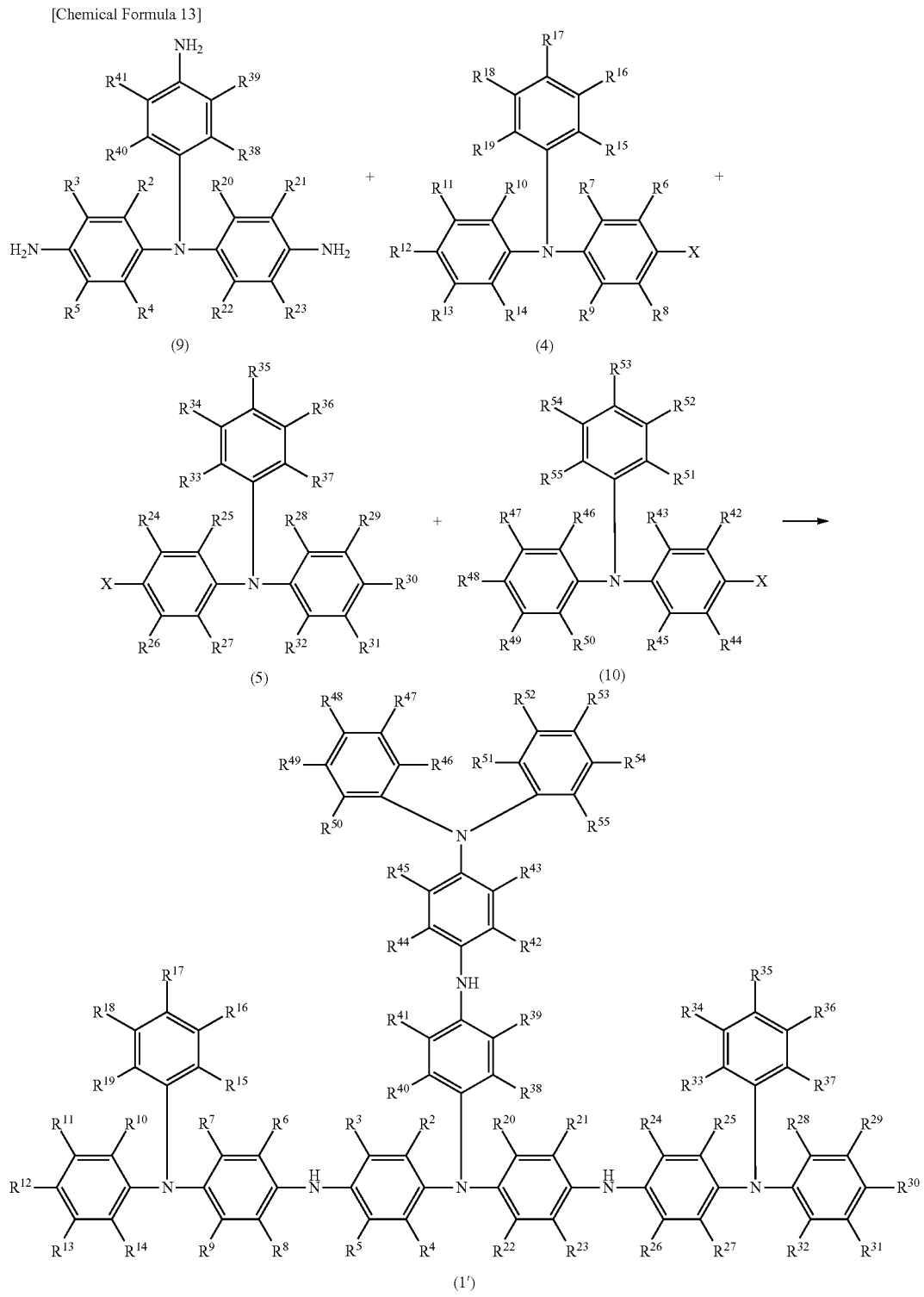
(wherein X and $R^1$ to $R^{55}$ are as defined above).

In Schemes 1 to 3, the halogen atoms represented by X are exemplified in the same way as indicated above. The pseudo-halogen group is exemplified by (fluoro)alkylsulfonyloxy groups such as methanesulfonyloxy, trifluoromethanesulfonyloxy and nanofluorobutanesulfonyloxy groups; and aromatic sulfonyloxy groups such as benzenesulfonyloxy and toluenesulfonyloxy groups.

Specific examples of the amine compound of formula (3) include N-methylbis(4-aminophenyl)amine and N,N-bis(p-aminophenyl)aniline, specific examples of the amine compound of formula (6) include N-methyl-bis(4-bromophenyl)amine and N,N-bis(p-bromophenyl)aniline, and specific examples of the amine compound of formula (9) include tris(4-aminophenyl)amine. However, these respective compounds are not limited to the examples given here.

The amine compounds of formulas (4), (5) and (10) are exemplified by 4'-bromo-N-phenyl-[1,1'-biphenyl]-4-amine, and the amine compounds of formulas (7) and (8) are exemplified by N,N-diphenyl-p-phenylenediamine. However, these respective compounds are not limited to the examples given here.

The charging ratio of the amine compound of formula (3) to the amine compounds of formulas (4) and (5), the charging ratio of the amine compound of formula (6) to the amine compounds of formulas (7) and (8), and the charging ratio of the amine compound of formula (9) to the amine compounds of formulas (4), (5) and (10) may be set to a molar ratio of 1 or more, with a molar ratio of about 1 to 1.2 being preferred.

The catalyst used in the reaction is exemplified by copper catalysts such as copper chloride, copper bromide and copper iodide; and palladium catalysts such as tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$) and bis(tri-t-butylphosphine)palladium ($Pd(P-t-Bu_3)_2$). These catalysts may be used singly or two or more may be used in combination. Also, these catalysts may be used together with suitable known ligands.

The amount of catalyst used may be set to about 0.001 to 0.2 mole per mole of the amine compound of formula (3), (6) or (9), with an amount of about 0.005 to 0.05 mole being preferred.

When ligands are used, the amount of ligands may be set to 0.1 to 5 equivalents, and preferably 1 to 4 equivalents, with respect to the metal complex used.

The reaction may be carried out in a solvent. The solvent is not particularly limited, provided it is one that does not adversely affect the reaction. Illustrative examples of the solvent include aliphatic hydrocarbons (pentane, n-hexane, n-octane, n-decane, decalin, etc.), halogenated aliphatic hydrocarbons (chloroform, dichloromethane, dichloroethane, carbon tetrachloride, etc.), aromatic hydrocarbons (benzene, nitrobenzene, toluene, o-xylene, m-xylene, p-xylene, mesitylene, etc.), halogenated aromatic hydrocarbons (chlorobenzene, bromobenzene, o-dichlorobenzene, m-dichlorobenzene, p-dichlorobenzene, etc.), ethers (diethyl ether, diisopropyl ether, t-butyl methyl ether, tetrahydrofuran, dioxane, 1,2-dimethoxyethane, 1,2-diethoxyethane, etc.), ketones (acetone, methyl ethyl ketone, methyl isobutyl ketone, di-n-butyl ketone, cyclohexanone, etc.), amides (N,N-dimethylformamide, N,N-dimethylacetamide, etc.), lactams and lactones (N-methylpyrrolidone, γ-butyrolactone, etc.), ureas (N,N-dimethylimidazolidinone, tetramethylurea, etc.), sulfoxides (dimethylsulfoxide, sulfolane, etc.), and nitriles (acetonitrile, propionitrile, butyronitrile, etc.). These solvents may be used singly, or two or more may be used in admixture.

The reaction temperature may be suitably set in the range of from the melting point to the boiling point of the solvent used, with a temperature of about 0° C. to 200° C. being preferred, and a temperature of 20 to 150° C. being more preferred.

Following reaction completion, the target aniline derivative can be obtained by work-up in the usual manner.

[Charge-Transporting Varnish]

The charge-transporting varnish of the invention includes a charge-transporting substance consisting of the aniline derivative of formula (1), and an organic solvent. In order to increase the charge transportability, etc., the varnish may also optionally include a dopant.

The dopant is not particularly limited, provided it is one that dissolves in at least one of the solvents used in the varnish; either an inorganic dopant or an organic dopant may be used.

Examples of inorganic dopants include inorganic acids such as hydrogen chloride, sulfuric acid, nitric acid and phosphoric acid; metal halides such as aluminum(III) chloride ($AlCl_3$), titanium(IV) tetrachloride ($TiCl_4$), boron tribromide ($BBr_3$), a boron trifluoride-ether complex ($BF_3.OEt_2$), iron(III) chloride ($FeCl_3$), copper(II) chloride ($CuCl_2$), antimony(V) pentachloride ($SbCl_5$), antimony(V) pentafluoride ($SbF_5$), arsenic(V) pentafluoride ($AsF_5$), phosphorus pentafluoride ($PF_5$) and tris(4-bromophenyl)aluminum hexachloroantimonate (TBPAH); halogens such as $Cl_2$, $Br_2$, $I_2$, ICl, $ICl_3$, IBr and $IF_4$; and heteropolyacids such as phosphomolybdic acid and phosphotungstic acid.

Examples of organic dopants include arylsulfonic acid compounds such as benzenesulfonic acid, tosylic acid, p-styrenesulfonic acid, 2-naphthalenesulfonic acid, 4-hydroxybenzenesulfonic acid, 5-sulfosalicyclic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalene-sulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, the 1,4-benzodioxanedisulfonic acid compounds mentioned in International Disclosure WO 2005/000832, the arylsulfonic acid compounds mentioned in International Disclosure WO 2006/025342, the arylsulfonic acid compounds mentioned in International Disclosure WO 2009/096352 and polystyrenesulfonic acid; non-arylsulfonic acid compounds such as 10-camphorsulfonic acid; and organic oxidizing agents such as 7,7,8,8-tetracyanoquinodimethane (TCNQ) and 2,3-dichloro-5,6-dicyano-1,4-benzoquinone (DDQ).

These inorganic and organic dopants may be used singly, or two or more may be used in combination.

Of these dopants, a heteropolyacid is preferred. By using a heteropolyacid as the dopant, it is possible to obtain a thin-film of excellent charge transportability that not only has a good ability to accept holes from transparent electrodes such as indium-tin oxide (ITO) or indium-zinc oxide (IZO), but also demonstrates a good ability to accept holes from metal anodes such as aluminum.

"Heteropolyacid" refers to a polyacid having a structure in which a heteroatom is positioned at the center of the molecule—typically the Keggin-type chemical structure shown in formula (B1) or the Dawson-type chemical structure shown in formula (B2), and which is obtained by the condensation of an isopolyacid that is an oxo acid of vanadium (V), molybdenum (Mo), tungsten (W) or the like with an oxo acid of a different element. Examples of such oxo acids of a different element include primarily oxo acids of silicon (Si), phosphorus (P) and arsenic (As).

[Chemical Formula 14]

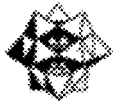

(B1)

(B2)

Examples of heteropolyacids include phosphomolybdic acid, silicomolybdic acid, phosphotungstic acid, silicotungstic acid and phosphotungstomolybdic acid. These may be used singly, or two or more may be used in combination. The heteropolyacid compound used in this invention may be acquired as a commercial product or may be synthesized by a known method.

When the dopant consists of a single heteropolyacid, this single heteropolyacid is preferably phosphotungstic acid or phosphomolybdic acid, and more preferably phosphotungstic acid. When the dopant consists of two or more heteropolyacids, at least one of the two or more heteropolyacids is preferably phosphotungstic acid or phosphomolybdic acid, and more preferably phosphotungstic acid.

Even a heteropolyacid having, in quantitative analysis such as elemental analysis, numbers for the elements which are higher or lower than in the structure indicated by the general formula may be used in this invention, provided it was acquired as a commercial product or was suitably synthesized according to a known method of synthesis.

For example, phosphotungstic acid is generally represented by the chemical formula $H_3(PW_{12}O_{40}) \cdot nH_2O$ and phosphomolybdic acid is generally represented by the chemical formula $H_3(PMo_{12}O_{40}) \cdot nH_2O$. In quantitative analysis, regardless of whether the numbers for the elements P (phosphorus), O (oxygen) and W (tungsten) or Mo (molybdenum) within these formulas are high or low, so long as the heteropolyacid was acquired as a commercial product or suitably synthesized by a known method of synthesis, it may be used in this invention. In such cases, the mass of the heteropolyacid specified in this invention refers not to the mass of pure phosphotungstic acid within the product of synthesis or the commercial product (phosphotungstic acid content), but rather, in the form that is available as a commercial product or the form that can be isolated by a known method of synthesis, to the total mass in a state that includes water of hydration and other impurities.

An arylsulfonic acid compound may also be advantageously used as the dopant. Arylsulfonic acid compounds of formula (11) or (12) are especially preferred.

[Chemical Formula 15]

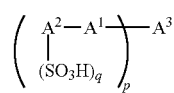

(11)

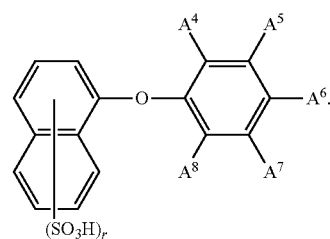

(12)

In formula (11), $A^1$ is —O— or —S—, with —O— being preferred. $A^2$ is a naphthalene ring or an anthracene ring, with a naphthalene ring being preferred. $A^3$ is a perfluorobiphenyl group having a valence of 2 to 4. The letter p represents the number of bonds between $A^1$ and $A^3$, this being an integer which satisfies the condition $2 \leq p \leq 4$. $A^3$ is preferably a divalent perfluorobiphenyl group, and p is preferably 2. The letter q represents the number of sulfonic acid groups that bond with $A^2$, this being an integer which satisfies the condition $1 \leq q \leq 4$, and preferably 2.

In formula (12), $A^4$ to $A^8$ are each independently a hydrogen atom, a halogen atom, a cyano group, an alkyl group of 1 to 20 carbon atoms, a halogenated alkyl group of 1 to 20 carbon atoms or a halogenated alkenyl group of 2 to 20 carbon atoms, with at least three from among $A^4$ to $A^8$ being halogen atoms. Also, r represents the number of sulfonic acid groups bonded to the naphthalene ring, this being an integer which satisfies the condition $1 \leq r \leq 4$, preferably 2 to 4, and more preferably 2.

Examples of the halogenated alkyl group of 1 to 20 carbon atoms include trifluoromethyl, 2,2,2-trifluoroethyl, 1,1,2,2,2-pentafluoroethyl, 3,3,3-trifluoropropyl, 2,2,3,3,3-pentafluoropropyl, 1,1,2,2,3,3,3-heptafluoropropyl, 4,4,4-trifluorobutyl, 3,3,4,4,4-pentafluorobutyl, 2,2,3,3,4,4,4-heptafluorobutyl and 1,1,2,2,3,3,4,4,4-nonafluorobutyl groups.

Examples of the halogenated alkenyl group of 2 to 20 carbon atoms include perfluorovinyl, 1-perfluoropropenyl, perfluoroallyl and perfluorobutenyl groups.

The halogen atom and the alkyl group of 1 to 20 carbon atoms are exemplified in the same way as above, with the halogen atom preferably being a fluorine atom.

Of these, $A^4$ to $A^8$ are preferably hydrogen atoms, halogen atoms, cyano groups, alkyl groups of 1 to 10 carbon atoms, halogenated alkyl groups of 1 to 10 carbon atoms, or halogenated alkenyl groups of 2 to 10 carbon atoms, with at least 3 from among $A^4$ to $A^8$ being fluorine atoms; more preferably hydrogen atoms, fluorine atoms, cyano groups, alkyl groups of 1 to 5 carbon atoms, fluorinated alkyl groups of 1 to 5 carbon atoms, or fluorinated alkenyl groups of 2 to 5 carbon atoms, with at least 3 from among $A^4$ to $A^8$ being fluorine atoms; and even more preferably hydrogen atoms, fluorine atoms, cyano groups, perfluoroalkyl groups of 1 to 5 carbon atoms, or perfluoroalkenyl groups of 1 to 5 carbon atoms, with $A^4$, $A^5$ and $A^8$ being fluorine atoms.

Here, "perfluoroalkyl group" refers to an alkyl group in which all the hydrogen atoms are substituted with fluorine atoms, and "perfluoroalkenyl group" refers to an alkenyl group in which all the hydrogen atoms are substituted with fluorine atoms.

Specific examples of arylsulfonic acid compounds preferred as other dopants in this invention include, but are not limited to, the following.

[Chemical Formula 16]

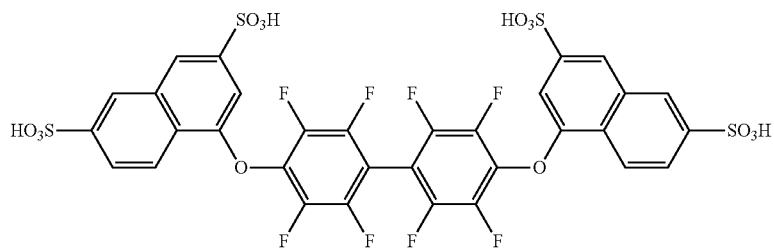
(b1)

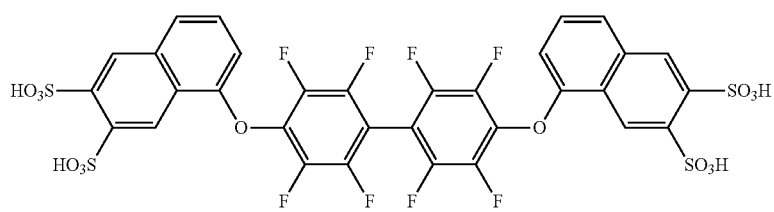
(b2)

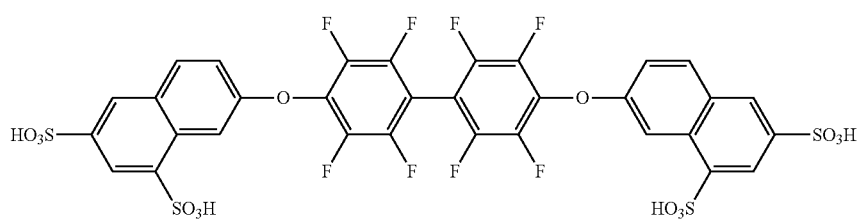
(b3)

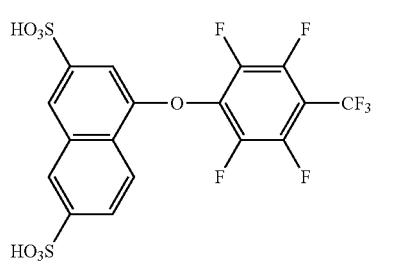
(b4)

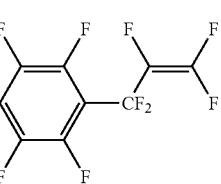
(b5)

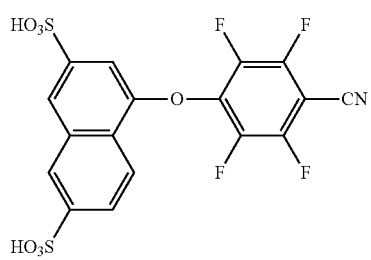
(b6)

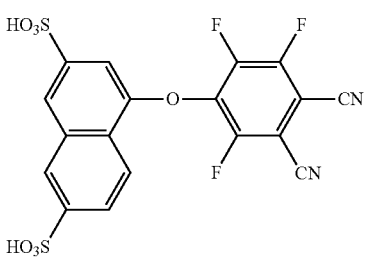
(b7)

When a dopant is included in the charge-transporting varnish of the invention, the amount of dopant used is set as appropriate based on such considerations as the type of dopant and the desired degree of charge transportability, and thus cannot be strictly specified. Typically, however, the dopant is included in a mass ratio with respect to unity (1) for the charge-transporting substance consisting of the inventive aniline derivative (referred to below as simply the "charge-transporting substance") in the range of generally about 0.01 to 50.

Specifically, when a heteropolyacid is used as the dopant, by setting the heteropolyacid to a mass ratio with respect to unity (1) for the charge-transporting substance of about 0.5 to 30.0, preferably about 1.0 to 20.0, more preferably about 2.0 to 15.0, even more preferably about 3.0 to 12.0, and still more preferably about 4.0 to 11.0, a charge-transporting thin-film that imparts a high brightness when used in organic EL devices can be reproducibly obtained.

On the other hand, when an arylsulfonic acid compound is used as the dopant, by setting the arylsulfonic acid compound to a mass ratio with respect to unity (1) for the charge-transporting substance of 0.05 to 15.0, preferably 0.10 to 10.0, more preferably 0.25 to 7.0, even more preferably 0.50 to 5.0, and still more preferably 0.75 to 3.0, a charge-transporting thin-film that imparts a high brightness when used in organic EL devices can be reproducibly obtained.

The charge-transporting varnish of the invention may additionally include an organosilane compound. By including an organosilane, the ability to inject holes into a layer that is stacked so as to be in contact with the hole injection layer on the side opposite from the anode—be it a hole transport layer or an emissive layer—can be increased, as a result of which even higher electrical characteristics can be achieved.

The organosilane compound is exemplified by dialkoxysilane compounds, trialkoxysilane compounds and tetraalkoxysilane compounds. These may be used singly, or two or more may be used in combination.

The organosilane compound is preferably a dialkoxysilane compound or a trialkoxysilane compound, and more preferably a trialkoxysilane compound.

The dialkoxysilane compound, trialkoxysilane compound and tetraalkoxysilane compound are exemplified by compounds of formulas (13) to (15).

$SiR'_2(OR)_2$ (13)

$SiR'(OR)_3$ (14)

$Si(OR)_4$ (15)

In the formulas, each R is independently an alkyl group of 1 to 20 carbon atoms which may be substituted with $Z^4$, an alkenyl group of 2 to 20 carbon atoms which may be substituted with $Z^4$, an alkynyl group of 2 to 20 carbon atoms which may be substituted with $Z^4$, an aryl group of 6 to 20 carbon atoms which may be substituted with $Z^5$, or a heteroaryl group of 2 to 20 carbon atoms which may be substituted with $Z^5$. Each R' is independently an alkyl group of 1 to 20 carbon atoms which may be substituted with $Z^6$, an alkenyl group of 2 to 20 carbon atoms which may be substituted with $Z^6$, an alkynyl group of 2 to 20 carbon atoms which may be substituted with $Z^6$, an aryl group of 6 to 20 carbon atoms which may be substituted with $Z^7$, or a heteroaryl group of 2 to 20 carbon atoms which may be substituted with $Z^7$.

$Z^4$ is a halogen atom, an aryl group of 6 to 20 carbon atoms which may be substituted with $Z^8$, or a heteroaryl group of 2 to 20 carbon atoms which may be substituted with $Z^8$.

$Z^5$ is a halogen atom, an alkyl group of 1 to 20 carbon atoms which may be substituted with $Z^8$, an alkenyl group of 2 to 20 carbon atoms which may be substituted with $Z^8$, or an alkynyl group of 2 to 20 carbon atoms which may be substituted with $Z^8$.

$Z^6$ is a halogen atom, an aryl group of 6 to 20 carbon atoms which may be substituted with $Z^8$, a heteroaryl group of 2 to 20 carbon atoms which may be substituted with $Z^8$, an epoxycyclohexyl group, a glycidoxy group, a methacryloxy group, an acryloxy group, a ureido group (—NHCONH$_2$), a thiol group, an isocyanate group (—NCO), an amino group, —NHY$^9$ or —NY$^{10}$Y$^{11}$.

$Z^7$ is a halogen atom, an alkyl group of 1 to 20 carbon atoms which may be substituted with $Z^8$, an alkenyl group of 2 to 20 carbon atoms which may be substituted with $Z^8$, an alkynyl group of 2 to 20 carbon atoms which may be substituted with $Z^8$, an epoxycyclohexyl group, a glycidoxy group, a methacryloxy group, an acryloxy group, a ureido group (—NHCONH$_2$), a thiol group, an isocyanate group (—NCO), an amino group, —NHY$^9$ or —NY$^{10}$Y$^{11}$.

$Y^9$ to $Y^{11}$ are each independently an alkyl group of 1 to 20 carbon atoms which may be substituted with $Z^8$, an alkenyl group of 2 to 20 carbon atoms which may be substituted with $Z^8$, an alkynyl group of 2 to 20 carbon atoms which may be substituted with $Z^8$, an aryl group of 6 to 20 carbon atoms which may be substituted with $Z^8$, or a heteroaryl group of 2 to 20 carbon atoms which may be substituted with $Z^8$.

$Z^8$ is a halogen atom, an amino group, a nitro group, a cyano group or a thiol group.

In formulas (13) to (15), the halogen atom, alkyl group of 1 to 20 carbon atoms, alkenyl group of 2 to 20 carbon atoms, alkynyl group of 2 to 20 carbon atoms, aryl group of 6 to 20 carbon atoms and heteroaryl group of 2 to 20 carbon atoms are exemplified in the same way as above.

In R and R', the number of carbon atoms on the alkyl, alkenyl and alkynyl groups is preferably 10 or less, more preferably 6 or less, and even more preferably 4 or less. Also, the number of carbon atoms on the aryl and heteroaryl groups is preferably 14 or less, more preferably 10 or less, and even more preferably 6 or less.

R is preferably an alkyl group of 1 to 20 carbon atoms or an alkenyl group of 2 to 20 carbon atoms which may be substituted with $Z^4$, or an aryl group of 6 to 20 carbon atoms which may be substituted with $Z^5$; more preferably an alkyl group of 1 to 6 carbon atoms or an alkenyl group of 2 to 6 carbon atoms which may be substituted with $Z^4$, or a phenyl group which may be substituted with $Z^5$; even more preferably an alkyl group of 1 to 4 carbon atoms which may be substituted with $Z^4$ or a phenyl group which may be substituted with $Z^5$; and still more preferably a methyl group or ethyl group which may be substituted with $Z^4$.

R' is preferably an alkyl group of 1 to 20 carbon atoms which may be substituted with $Z^6$, or an aryl group of 6 to 20 carbon atoms which may be substituted with $Z^7$; more preferably an alkyl group of 1 to 10 carbon atoms which may be substituted with $Z^6$, or an aryl group of 6 to 14 carbon atoms which may be substituted with $Z^7$; even more preferably an alkyl group of 1 to 6 carbon atoms which may be substituted with $Z^6$, or an aryl group of 6 to 10 carbon atoms which may be substituted with $Z^7$; and still more preferably an alkyl group of 1 to 4 carbon atoms which may be substituted with $Z^6$, or a phenyl group which may be substituted with $Z^7$.

The plurality of R moieties may all be the same or different, and the plurality of R' moieties may likewise all be the same or different.

$Z^4$ is preferably a halogen atom or an aryl group of 6 to 20 carbon atoms which may be substituted with $Z^8$, more preferably a fluorine atom or a phenyl group which may be substituted with $Z^8$, and most preferably does not exist (i.e., is non-substituting).

$Z^5$ is preferably a halogen atom or an alkyl group of 6 to 20 carbon atoms which may be substituted with $Z^8$, more preferably a fluorine atom or an alkyl of 1 to 10 carbon atoms which may be substituted with $Z^8$, and most preferably does not exist (i.e., is non-substituting).

$Z^6$ is preferably a halogen atom, a phenyl group which may be substituted with $Z^8$, a furanyl group which may be substituted with $Z^8$, an epoxycyclohexyl group, a glycidoxy group, a methacryloxy group, an acryloxy group, a ureido group, a thiol group, an isocyanate group, an amino group, a phenylamino group which may be substituted with $Z^8$, or a diphenylamino group which may be substituted with $Z^8$; more preferably a halogen atom; and even more preferably a fluorine atom or does not exist (i.e., is non-substituting).

$Z^7$ is preferably a halogen atom, an alkyl group of 1 to 20 carbon atoms which may be substituted with $Z^8$, a furanyl group which may be substituted with $Z^8$, an epoxycyclohexyl group, a glycidoxy group, a methacryloxy group, an acryloxy group, a ureido group, a thiol group, an isocyanate group, an amino group, a phenylamino group which may be substituted with $Z^8$, or a diphenylamino group which may be substituted with $Z^8$; more preferably a halogen atom; and even more preferably a fluorine atom or does not exist (i.e., is non-substituting).

$Z^8$ is preferably a halogen atom, and more preferably a fluorine atom or does not exist (i.e., is non-substituting).

Examples of organosilane compounds that may be used in this invention include, but are not limited to, the following.

Specific examples of dialkoxysilane compounds include dimethyldimethoxysilane, dimethyldiethoxysilane, methylethyldimethoxysilane, diethyldimethoxysilane, diethyldiethoxysilane, methylpropyldimethoxysilane, methylpropyldiethoxysilane, diisopropyldimethoxysilane, phenylmethyldimethoxysilane, vinylmethyldimethoxysilane, 3-glycidoxypropylmethyldimethoxysilane, 3-glycidoxypropylmethyldiethoxysilane, 3-(3,4-epoxycyclohexyl)ethylmethyldimethoxysilane, 3-methacryloxypropylmethyldimethoxysilane, 3-methacryloxypropylmethyldiethoxysilane, 3-mercaptopropylmethyldimethoxysilane, γ-aminopropylmethyldiethoxysilane, N-(2-aminoethyl)aminopropylmethyldimethoxysilane and 3,3,3-trifluoropropylmethyldimethoxysilane.

Specific examples of trialkoxysilane compounds include methyltrimethoxysilane, methyltriethoxysilane, ethyltrimethoxysilane, ethyltriethoxysilane, propyltrimethoxysilane, propyltriethoxysilane, butyltrimethoxysilane, butyltriethoxysilane, pentyltrimethoxysilane, pentyltriethoxysilane, heptyltrimethoxysilane, heptyltriethoxysilane, octyltrimethoxysilane, octyltriethoxysilane, dodecyltrimethoxysilane, dodecyltriethoxysilane, hexadecyltrimethoxysilane, hexadecyltriethoxysilane, ootadecyltrimethoxysilane, octadecyltriethoxysilane, phenyltrimethoxysilane, phenyltriethoxysilane, vinyltrimethoxysilane, vinyltriethoxysilane, γ-aminopropyltrimethoxysilane, 3-aminopropyltriethoxysilane, γ-glycidoxypropyltrimethoxysilane, 3-glycidoxypropyltriethoxysilane, γ-methacryloxypropyltrimethoxysilane, γ-methacryloxypropyltriethoxysilane, triethoxy(4-(trifluoromethyl)phenyl)silane, dodecyltriethoxysilane, 3,3,3-trifluoropropyltrimethoxysilane, (triethoxysilyl)cyclohexane, perfluorooctylethyltriethoxysilane, triethoxyfluorosilane, tridecafluoro-1,1,2,2,-tetrahydrooctyltriethoxysilane, pentafluorophenyltrimethoxysilane, pentafluorophenyltriethoxysilane, 3-(heptafluoroisopropoxy)propyltriethoxysilane, heptadecafluoro-1,1,2,2-tetrahydrodecyltriethoxysilane, triethoxy-2-thienylsilane and 3-(triethoxysilyl)furan.

Specific examples of tetraalkoxysilane compounds include tetramethoxysilane, tetraethoxysilane and tetrapropoxysilane.

Of these, 3,3,3-trifluoropropylmethyldimethoxysilane, triethoxy(4-(trifluoromethyl)phenyl)silane, 3,3,3-trifluoropropyltrimethoxysilane, perfluorooctylethyltriethoxysilane, pentafluorophenyltrimethoxysilane and pentafluorophenyltriethoxysilane are preferred.

When an organosilane compound is included in the charge-transporting varnish of the invention, to maintain a high charge transportability in the thin-film obtained therefrom, the content of the organosilane compound, based on the total mass of the charge-transporting substance and the dopant, is generally about 0.1 to 50 mass %. However, to suppress a decrease in the charge transportability of the thin-film and also increase the ability to inject holes in a layer that is stacked so as to be in contact with the hole injection layer on the side opposite from the anode—be it a hole transport layer or an emissive layer, the content is preferably about 0.5 to 40 mass %, more preferably about 0.8 to 30 mass %, and even more preferably about 1 to 20 mass %.

In addition to a charge-transporting substance consisting of the above-described aniline derivative, the charge-transporting varnish of the invention may include also a known charge-transporting substance.

Highly solvating solvents which are capable of dissolving well the charge-transporting substance and the dopant may be used as the organic solvent employed when preparing the charge-transporting varnish.

Examples of such highly solvating solvents that may be used include organic solvents such as N,N-dimethylformamide, N,N-dimethylacetamide, N-methylpyrrolidone, 1,3-dimethyl-2-imidazolidinone and diethylene glycol monomethyl ether. These solvents may be used singly, or two or more may be used in admixture. The amount thereof may be set to 5 to 100 mass %, based on the overall solvent used in the varnish.

The charge-transporting substance and dopant are preferably in a state where both are either completely dissolved or uniformly dispersed in the solvent; and are more preferably completely dissolved.

In the practice of the invention, by including in the varnish at least one high-viscosity organic solvent having a viscosity at 25° C. of 10 to 200 mPa·s, especially 35 to 150 mPa·s, and a boiling point at standard pressure (atmospheric pressure) of 50 to 300° C., especially 150 to 250° C., the viscosity of the varnish is easily adjusted, thus making it possible to prepare a varnish which reproducibly gives thin-films of high flatness and is suitable for the coating method to be used.

Examples of high-viscosity organic solvents include, but are not particularly limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. These solvents may be used singly, or two or more may be used in admixture.

The amount of high-viscosity organic solvent added as a proportion of the overall solvent used in the varnish of the invention is preferably within a range where no precipitation of solids occurs. The amount of such addition is preferably 5 to 80 mass %, provided that no precipitation of solids occurs.

In addition, other solvents may be admixed in a proportion with respect to the overall solvent used in the varnish of 1 to 90 mass %, and preferably 1 to 50 mass %, for such purposes as to enhance the substrate wettability by the varnish, adjust the solvent surface tension, adjust the polarity, and adjust the boiling point.

Examples of such solvents include, but are not limited to, propylene glycol monomethyl ether, ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly, or two or more may be used in admixture.

The viscosity of the inventive varnish is set as appropriate for the thickness and other properties of the thin-film to be produced and the solids concentration of the varnish, but is generally from 1 to 50 mPa·s at 25° C.

The solids concentration of the charge-transporting varnish of this invention is set as appropriate based on such considerations as the viscosity, surface tension and other properties of the varnish and the thickness and other properties of the thin-film to be produced, and is generally about 0.1 to 10.0 mass %. To improve the coating properties of the varnish, the solids concentration of the varnish is preferably 0.5 to 5.0 mass %, and more preferably 1.0 to 3.0 mass %.

A charge-transporting thin-film can be formed on a substrate by coating the inventive charge-transporting varnish onto the substrate and baking.

Examples of the varnish coating method include, but are not particularly limited to, dipping, spin coating, transfer printing, roll coating, brush coating, inkjet printing, spraying and slit coating. The viscosity and surface tension of the varnish are preferably adjusted according to the coating method to be used.

When using the varnish of the invention, the baking atmosphere is not particularly limited. A thin-film having a uniform film surface and high charge transportability can be obtained not only in an open-air atmosphere, but even in an inert gas such as nitrogen or in a vacuum.

The baking temperature is suitably set in a range of generally about 100 to 260° C. while taking into account such factors as the intended use of the resulting thin-film and the degree of charge transportability to be imparted to the thin-film. When the thin-film thus obtained is to be used as a hole injection layer in an organic EL device, the baking temperature is preferably about 140 to 250° C., and more preferably about 145 to 240° C.

During baking, a temperature change in two or more steps may be applied for such purposes as to achieve more uniform film formability or to induce the reaction to proceed on the substrate. Heating may be carried out using a suitable apparatus such as a hot plate or an oven.

The thickness of the charge-transporting thin-film is not particularly limited. However, when the thin-film is to be used as a hole injection layer in an organic EL device, a film thickness of 5 to 200 nm is preferred. Methods for changing the film thickness include, for example, changing the solids concentration in the varnish and changing the amount of solution on the substrate during coating.

[Organic EL Device]

The materials and method employed to fabricate organic light-emitting diode (OLED) devices using the charge-transporting varnish of the invention are exemplified by, but not limited to, those mentioned below.

The electrode substrate to be used is preferably cleaned beforehand by liquid washing with, for example, a cleaning agent, alcohol or pure water. When the substrate is an anode substrate, it is preferably subjected to surface treatment such as UV/ozone treatment or oxygen-plasma treatment just prior to use. However, surface treatment need not be carried out if the anode material is composed primarily of organic substances.

A method of manufacturing an OLED device having a hole injection layer made of a thin-film obtained from the charge-transporting varnish of the invention is described below by way of illustration.

In the manner described above, a hole injection layer is formed on an electrode by coating the charge-transporting varnish of the invention onto an anode substrate and baking. The workpiece is then introduced into a vacuum deposition system, where a hole transport layer, emissive layer, electron transport layer, electron transport layer/hole-blocking layer and cathode metal are vapor-deposited in this order to form the OLED device. Where necessary, an electron-blocking layer may be provided between the emissive layer and the hole transport layer.

Illustrative examples of anode materials include transparent electrodes such as indium-tin oxide (ITO) and indium-zinc oxide (IZO), and metal anodes made of a metal such as aluminum or an alloy of such a metal. An anode material on which planarizing treatment has been carried out is preferred. Use can also be made of polythiophene derivatives and polyaniline derivatives having high charge transportability.

Examples of other metals making up the metal anode include, but are not limited to, scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof.

Specific examples of hole transport layer-forming materials include triarylamines such as (triphenylamine) dimer derivatives, [(triphenylamine) dimer]spirodimer, N,N'-bis(naphthalen-1-yl)-N,N'-bis(phenyl)benzidine (α-NPD), N,N'-bis(naphthalen-2-yl)-N,N'-bis(phenyl)benzidine, N,N'-bis(3-methylphenyl)-N,N'-bis(phenyl)benzidine, N,N'-bis(3-methylphenyl)-N,N'-bis(phenyl)-9,9-spirobifluorene, N,N'-bis(naphthalen-1-yl)-N,N'-bis(phenyl)-9,9-spirobifluorene, N,N'-bis(3-methylphenyl)-N,N'-bis(phenyl)-9,9-dimethylfluorene, N,N'-bis(naphthalen-1-yl)-N,N'-bis(phenyl)-9,9-dimethylfluorene, N,N'-bis(3-methylphenyl)-N,N'-bis(phenyl)-9,9-diphenylfluorene, N,N'-bis(naphthalen-1-yl)-N,N'-bis(phenyl)-9,9-diphenylfluorene, N,N'-bis(naphthalen-1-yl)-N,N'-bis(phenyl)-2,2'-dimethylbenzidine, 2,2',7,7'-tetrakis(N,N-diphenylamino)-9,9-spirobifluorene, 9,9-bis[4-(N,N-bisbiphenyl-4-ylamino)phenyl]-9H-fluorene, 9,9-bis[4-(N,N-bisnaphthalen-2-ylamino)phenyl]-9H-fluorene, 9,9-bis[4-(N-naphthalen-1-yl-N-phenylamino)phenyl]-9H-fluorene, 2,2',7,7'-tetrakis[N-naphthalenyl(phenyl)amino]-9,9-spiro-bifluoene, N,N'-bis(phenanthren-9-yl)-N,N'-bis(phenyl)benzidine, 2,2'-bis[N,N-bis(biphenyl-4-yl)amino]-9,9-spirobifluorene, 2,2'-bis(N,N-diphenylamino)-9,9-spirobifluorene, di[4-(N,N-di(p-tolyl)amino)phenyl]cyclohexane, 2,2',7,7'-tetra(N,N-di(p-tolyl))amino-9,9-spirobifluorene, N,N,N',N'-tetranaphthalen-2-ylbenzidine, N,N,N',N'-tetra(3-methylphenyl)-3,3'-dimethylbenzidine, N,N'-di(naphthalenyl)-N,N'-di(naphthalen-2-yl)benzidine, N,N,N',N'-tetra(naphthalenyl)benzidine, N,N'-di(naphthalen-2-yl)-N,N'-diphenylbenzidine-1-4-diamine, $N^1,N^4$-diphenyl-$N^1$,$N^4$-di(m-tolyl)benzene-1,4-diamine, $N^2,N^2,N^6,N^6$-tetraphenylnaphthalene-2,6-diamine, tris(4-(quinolin-8-yl)phenyl)amine, 2,2'-bis(3-(N,N-di(p-tolyl)amino)phenyl)biphenyl, 4,4',4''-tris[3-methylphenyl(phenyl)amino]triphenylamine (m-MTDATA) and 4,4',4''-tris[1-naphthyl(phenyl)amino]triphenylamine (1-TNATA); and oligothiophenes such as 5,5''-bis-{4-[bis(4-methylphenyl)amino]phenyl}-2,2':5',2''-terthiophene (BMA-3T).

Specific examples of emissive layer-forming materials include tris(8-quinolinolate) aluminum(III) ($Alq_3$), bis(8-quinolinolate) zinc(II) ($Znq_2$), bis(2-methyl-8-quinolinolate)(p-phenylphenolate) aluminum(III) (BAlq), 4,4'-bis(2,2-diphenylvinyl)biphenyl, 9,10-di(naphthalen-2-yl)anthracene, 2-t-butyl-9,10-di(naphthalen-2-yl)anthracene, 2,7-bis[9,9-di(4-methylphenyl)fluoren-2-yl]-9,9-di(4-methyl-phenyl)fluorene, 2-methyl-9,10-bis(naphthalen-2-yl)anthracene, 2-(9,9-spirobifluoren-2-yl)-9,9-spirobifluorene, 2,7-bis(9,9-spirobifluoren-2-yl)-9,9-spirobifluorene, 2-[9,9-di(4-methylphenyl)fluoren-2-yl]-9,9-di(4-methylphenyl)fluorene, 2,2'-dipyrenyl-9,9-spirobifluorene, 1,3,5-tris(pyren-1-yl)benzene, 9,9-bis[4-(pyrenyl)phenyl]-9H- fluorene, 2,2'-bi(9,10-diphenylanthracene), 2,7-dipyrenyl-9,9-spirobifluorene, 1,4-di(pyren-1-yl)benzene, 1,3-di(pyren-1-yl)benzene, 6,13-di(biphenyl-4-yl)pentacene, 3,9-di(naphthalen-2-yl)-perylene, 3,10-di(naphthalen-2-yl)perylene, tris[4-(pyrenyl)phenyl]amine, 10,10'-di(biphenyl-4-yl)-9,9'-bianthracene, N,N'-di(naphthalen-1-yl)-N,N'-diphenyl[1,1':4',1":4",1"'-quaterphenyl]-4,4"'-diamine, 4,4'-di[10-(naphthalen-1-yl)anthracen-9-yl]biphenyl, dibenzo{[f,f']-4,4',7,7'-tetraphenyl}diindeno[1,2,3-cd:1',2',3'-lm]perylene, 1-(7-(9,9'-bianthracen-10-yl)-9,9-dimethyl-9H-fluoren-2-yl)-pyrene, 1-(7-(9,9'-bianthracen-10-yl)-9,9-dihexyl-9H-fluoren-2-yl)-pyrene, 1,3-bis(carbazol-9-yl)benzene, 1,3,5-tris(carbazol-9-yl)benzene, 4,4',4"-tris(carbazol-9-yl)triphenylamine, 4,4'-bis(carbazol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorene, 9,9-bis[4-(carbazol-9-yl)phenyl]fluorene, 2,7-bis(carbazol-9-yl)-9,9-spirobifluorene, 1,4-bis(triphenylsilyl)benzene, 1,3-bis(triphenylsilyl)benzene, bis(4-N,N-diethylamino-2-methylphenyl)-4-methylphenylmethane, 2,7-bis(carbazol-9-yl)-9,9-dioctylfluorene, 4,4"-di(triphenylsilyl)-p-terphenyl, 4,4'-di(triphenylsilyl)biphenyl, 9-(4-t-butylphenyl)-3,6-bis(triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benzo[d]imidazol-2-yl)phenyl-9H-fluoren-2-amine, 3,5-bis(3-(9H-carbazol-9-yl)phenyl)pyridine, 9,9-spirobifluoren-2-yldiphenylphosphine oxide, 9,9'-(5-triphenylsilyl)-1,3-phenylene)bis(9H-carbazole), 3-(2,7-bis(diphenylphosphoryl)-9-phenyl-9H-fluoren-9-yl)-9-phenyl-9H-carbazole, 4,4,8,8,12,12-hexa(p-tolyl)-4H-8H-12H-12C-azadibenzo[cd,mn]-pyrene, 4,7-di(9H-carbazol-9-yl)-1,10-phenanthroline, 2,2'-bis(4-(carbazol-9-yl)phenyl)biphenyl, 2,8-bis(diphenylphosphoryl)dibenzo[b,d]thiophene, bis(2-methylphenyl)diphenylsilane, bis[3,5-di(9H-carbazol-9-yl)phenyl]diphenylsilane, 3,6-bis(carbazol-9-yl)-9-(2-ethylhexyl)-9H-carbazole, 3-(diphenylphosphoryl)-9-(4-(diphenylphosphoryl)phenyl)-9H-carbazole and 3,6-bis[(3,5-diphenyl)phenyl]-9-phenyl-carbazole. It is also possible to form the emissive layer by co-vapor deposition of any of these materials with a light-emitting dopant.

Specific examples of light-emitting dopants include 3-(2-benzothiazolyl)-7-(diethylamino)coumarin, 2,3,6,7-tetrahydro-1,1,7,7-tetramethyl-1H,5H,11H-10-(2-benzothiazolyl)quinolidino[9,9a,1gh]coumarin, quinacridone, N,N'-dimethylquinacridone, tris(2-phenylpyridine) (Ir(ppy)$_3$), bis(2-phenylpyridine)(acetylacetonate) iridium(III) (Ir(ppy)$_2$(acac)), tris[2-(p-tolyl]pyridine) (Ir(mppy)$_3$), 9,10-bis[N,N-di(p-tolyl)amino]anthracene, 9,10-bis[phenyl(m-tolyl)amino]anthracene, bis[2-(2-hydroxyphenyl)benzothiazolate] zinc(II), $N^{10},N^{10},N^{10'},N^{10'}$-tetra(p-tolyl)-9,9'-bianthracene-10,10'-diamine, $N^{10},N^{10},N^{10'},N^{10'}$-tetraphenyl-9,9'-bianthracene-10,10'-diamine, $N^{10},N^{10'}$-diphenyl-$N^{10},N^{10'}$-dinaphthalenyl-9,9'-bianthracene-10,10'-diamine, 4,4'-bis(9-ethyl-3-carbazovinylene)-1,1'-biphenyl, perylene, 2,5,8,11-tetra-t-butylperylene, 1,4-bis[2-(3-N-ethylcarbazolyl)vinyl]benzene, 4,4'-bis[4-(di-p-tolylamino)styryl]biphenyl, 4-(di-p-tolylamino)-4'-[(di-p-tolylamino)styryl]stilbene, bis[3,5-difluoro-2-(2-pyridyl)phenyl-(2-carboxypyridyl)]iridium(III), 4,4'-bis[4-(diphenylamino)styryl]biphenyl, bis(2,4-difluorophenylpyridinato)tetrakis(1-pyrazolyl)borate iridium(III), N,N'-bis(naphthalen-2-yl)-N,N'-bis(phenyl)tris(9,9-dimethylfluorenylene), 2,7-bis{2-[phenyl(m-tolyl)amino]-9,9-dimethylfluoren-7-yl}-9,9-dimethylfluorene, N-(4-((E)-2-(6((E)-4-(diphenylamino)styryl)naphthalen-2-yl)vinyl)phenyl)-N-phenylbenzenamine, fac-iridium(III) tris(1-phenyl-3-methylbenzimidazolin-2-ylidene-C,C$^2$), mer-iridium(III) tris(1-phenyl-3-methylbenzimidazolin-2-ylidene-C,C$^2$), 2,7-bis[4-(diphenylamino)styryl]-9,9-spirobifluorene, 6-methyl-2-(4-(9-(4-(6-methylbenzo[d]thiazol-2-yl)phenyl)-anthracen-10-yl)phenyl)benzo[d]thiazole, 1,4-di[4-(N,N-diphenyl)amino]styrylbenzene, 1,4-bis(4-(9H-carbazol-9-yl)styryl)benzene, (E)-6-(4-(diphenylamino)styryl)-N,N-diphenylnaphthalen-2-amine, bis(2,4-difluorophenylpyridinato)(5-(pyridin-2-yl)-1H-tetrazolate) iridium(III), bis(3-trifluoromethyl-5-(2-pyridyl)pyrazole)((2,4-difluorobenzyl)diphenylphosphinate) iridium(III), bis(3-trifluoromethyl-5-(2-pyridyl)pyrazolate)(benzyl-diphenylphosphinate) iridium(III), bis(1-(2,4-difluorobenzyl)-3-methylbenzimidazolium)(3-(trifluoromethyl)-5-(2-pyridyl)-1,2,4-triazolate) iridium(III), bis(3-trifluoromethyl-5-(2-pyridyl)pyrazolate)(4',6'-difluorophenylpyridinate) iridium (III), bis(4',6'-difluorophenylpyridinato)(3,5-bis(trifluoromethyl)-2-(2'-pyridyl)pyrrolate) iridium(III), bis(4',6'-difluorophenylpyridinato)(3-(trifluoromethyl)-5-(2-pyridyl)-1,2,4-triazolate) iridium (III), (Z)-6-mesityl-N-(6-mesitylquinolin-2(1H)-ylidene)quinoline-2-amine-BF$_2$, (E)-2-(2-(4-(dimethylamino)styryl)-6-methyl-4H-pyran-4-ylidene)malononitrile, 4-(dicyanomethylene)-2-methyl-6-julolidyl-9-enyl-4-H-pyran, 4-(dicyanomethylene)-2-methyl-6-(1,1,7,7-tetramethyl-julolidyl-9-enyl)-4H-pyran, 4-(dicyanomethylene)-2-t-butyl-6-(1,1,7,7-tetramethyl-julolidin-4-ylvinyl)-4H-pyran, tris(dibenzoylmethane) phenanthroline europium(III), 5,6,11,12-tetraphenylnaphthacene, bis(2-benzo[b]thiophen-2-yl-pyridine)(acetylacetonate) iridium(III), tris(1-phenylisoquinoline) iridium(III), bis(1-phenylisoquinoline)(acetylacetonate) iridium(III), bis[1-(9,9-dimethyl-9H-fluoren-2-yl)isoquinoline]-(acetylacetonate) iridium(III), bis[2-(9,9-dimethyl-9H-fluoren-2-yl)quinoline]-(acetylacetonate) iridium(III), tris[4,4'-di-t-butyl-(2,2')-bipyridine]ruthenium(III)•bis(hexafluorophosphate), tris(2-phenylquinoline) iridium(III), bis(2-phenylquinoline)(acetylacetonate) iridium(III), 2,8-di-t-butyl-5,11-bis(4-t-butylphenyl)-6,12-diphenyltetracene, bis(2-phenylbenzothiazolate)(acetylacetonate) iridium(III), platinum 5,10,15,20-tetraphenyltetrabenzoporphyrin, osmium(II) bis(3-trifluoromethyl-5-(2-pyridine)pyrazolate)-dimethylphenylphosphine, osmium(II) bis(3-trifluoromethyl)-5-(4-t-butylpyridyl)-1,2,4-triazolate) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-t-butylpyridyl)-1,2,4-triazolate) dimethylphenylphosphine, bis[2-(4-n-hexylphenyl)quinoline](acetylacetonate) iridium(III), tris[2-(4-n-hexylphenyl)quinoline]iridium(III), tris[2-phenyl-4-methylquinoline]iridium(III), bis(2-phenylquinoline)(2-(3-methylphenyl)pyridinate) iridium(III), bis(2-(9,9-diethylfluoren-2-yl)-1-phenyl-1H-benzo[d]-imidazolato) (acetylacetonate) iridium(III), bis(2-phenylpyridlne)(3-(pyridin-2-yl)-2H-chromen-9-onate) iridium(III), bis(2-phenylquinoline)(2,2,6,6-tetramethylheptane-3,5-dionate) iridium(III), bis(phenylisoquinoline)(2,2,6,6-tetramethylheptane-3,5-dionate) iridium (III), iridium(III) bis(4-phenylthieno[3,2-c]pyridinato-N,C$^2$)acetylacetonate, (E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)- malononitrile, bis(3-trifluoromethyl-5-(1-isoquinolyl) pyrazolate)(methyl-diphenylphosphine) ruthenium, bis[(4-n-hexylphenyl)isoquinoline](acetylacetonate) iridium(III), platinum(II) octaethylporphin, bis(2-methyldibenzo[f,h]quinoxaline)(acetylacetonate) iridium(III) and tris[(4-n-hexylphenyl)isoquinoline]iridium(III).

Specific examples of electron transport layer/hole-blocking layer-forming materials include lithium 8-hydroxyquinolinate, 2,2',2''-(1,3,5-benzinetriyl)-tris(1-phenyl-1-H-benzimidazole), 2-(4-biphenyl)-5-(4-t-butylphenyl)-1,3,4-oxadiazole, 2,9-dimethyl-4,7-diphenyl-1,10-phenanthroline, 4,7-diphenyl-1,10-phenanthroline, bis(2-methyl-8-quinolinolate)-4-(phenylphenolato)aluminum, 1,3-bis[2-(2,2'-bipyridin-6-yl)-1,3,4-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo[4,5f]-[1,10]phenanthroline, 2-(naphthalen-2-yl)-4,7-diphenyl-1,10-phenanthroline, phenyldipyrenylphosphine oxide, 3,3',5,5'-tetra[(m-pyridyl)phen-3-yl]biphenyl, 1,3,5-tris[3-pyridyl]phen-3-yl]benzene, 4,4'-bis(4,6-diphenyl-1,3,5-triazin-2-yl)biphenyl, 1,3-bis[3,5-di(pyridin-3-yl)phenyl]benzene, bis(10-hydroxybenzo[h]quinolinato)beryllium, diphenylbis(4-(pyridin-3-yl)phenyl)silane and 3,5-di(pyren-1-yl)pyridine.

Examples of electron injection layer-forming materials include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), lithium acetate and lithium benzoate.

Examples of cathode materials include aluminum, magnesium-silver alloys, aluminum-lithium alloys, lithium, sodium, potassium and cesium.

An example of an electron-blocking layer-forming material is tris(phenylpyrazole) iridium.

The manufacture of polymer LED (PLED) devices using the charge-transporting varnish of the invention, although not particularly limited, is exemplified by the following method.

A PLED device having a charge-transporting thin-film formed using the charge-transporting varnish of the invention can be manufactured by, in the production of an OLED device as described above, successively forming a hole-transporting polymer layer and a light-emitting polymer layer instead of carrying out vacuum deposition operations for a hole transport layer, an emissive layer, an electron transport layer and an electron injection layer.

Specifically, the charge-transporting varnish of the invention is coated onto an anode substrate and a hole injection layer is formed by the above-described method. A hole-transporting polymer layer and a light-emitting polymer layer are then successively formed thereon, following which a cathode material is vapor-deposited on top, thereby forming the PLED device.

The cathode and anode materials used here may be similar to those used when producing an OLED device as described above, and similar cleaning treatment and surface treatment may be carried out.

The method of forming the hole-transporting polymer layer and the light-emitting polymer layer is exemplified by a film-forming method in which a solvent is added to a hole-transporting polymer material or a light-emitting polymer material, or a material obtained by adding thereto a dopant, thereby dissolving or uniformly dispersing the material, following which the resulting solution or dispersion is coated onto the hole injection layer or hole-transporting polymer layer and subsequently baked.

Examples of hole-transporting polymer materials include poly[(9,9-dihexylfluorenyl-2,7-diyl)-co-(N,N'-bis{p-butylphenyl}-1,4-diaminophenylene)], poly[(9,9-dioctylfluorenyl-2,7-diyl)-co-(N,N'-bis{p-butylphenyl}-1,1'-biphenylene-4,4-diamine)], poly[(9,9-bis{1'-penten-5'-yl}fluorenyl-2,7-diyl)-co-(N,N'-bis{p-butylphenyl}-1,4-diaminophenylene)], poly[N,N'-bis(4-butylphenyl)-N,N'-bis(phenyl)benzidine]end-capped with polysilsesquioxane and poly[(9,9-dioctylfluorenyl-2,7-diyl)-co-(4,4'-(N-(p-butylphenyl))diphenylamine)].

Examples of light-emitting polymer materials include polyfluorene derivatives such as poly(9,9-dialkylfluorene) (PDAF), poly(phenylene vinylene) derivatives such as poly (2-methoxy-5-(2'-ethylhexoxy)-1,4-phenylene vinylene) (MEH-PPV), polythiophene derivatives such as poly(3-alkylthiophene) (PAT), and polyvinylcarbazole (PVCz).

Examples of the solvent include toluene, xylene and chloroform. Examples of the method of dissolution or uniform dispersion include stirring, stirring under applied heat, and ultrasonic dispersion.

Examples of the coating method include, but are not particularly limited to, inkjet printing, spraying, dipping, spin coating, transfer printing, roll coating and brush coating. Coating is preferably carried out in an inert gas atmosphere such as nitrogen or argon.

Examples of the baking method include methods that involve heating in an oven or on a hot plate, either within an inert gas atmosphere or in a vacuum.

In addition, given that not only charge-transporting thin-films obtained from the above charge-transporting varnishes, but also vapor-deposited films obtained from the aniline derivatives of the invention have excellent charge transportability, depending on the intended application, use can be made of a charge-transporting thin-film obtained by vapor deposition.

EXAMPLES

Synthesis Examples and Working Examples are given below to more concretely illustrate the invention, although the invention is not limited by these Examples. The equipment used was as follows.
(1) MALDI-TOF-MS: Autoflex III SmartBeam, from Bruker Daltonics
(2) $^1$H-NMR Measurement: JNM-ECP300 FT NMR System, from JEOL, Ltd.
(3) Substrate Cleaning: Substrate cleaning machine (reduced-pressure plasma system), from Choshu Industry Co., Ltd.
(4) Varnish Coating: MS-A100 Spin Coater, from Mikasa Co., Ltd.
(5) Film Thickness Measurement: Surfcorder ET-4000 microfigure measuring instrument, from Kosaka Laboratory, Ltd.
(6) EL Device Fabrication: C-E2L1G1-N Multifunction Vapor Deposition System, from Choshu Industry Co., Ltd.
(7) Measurement of EL Device Brightness, etc.: I-V-L Measurement System from Tech World, Inc.

(8) EL Device Lifetime Measurement (half-life measurement): PEL-105S Organic EL Brightness Life Evaluation System, from EHC K.K.

[Synthesis Example 1] Synthesis of Arylsulfonic Acid Compound 1

Arylsulfonic Acid Compound 1 (formula (b1)) was synthesized by the following reaction, based on the description provided in International Disclosure WO 2006/025342.

[Chemical Formula 17]

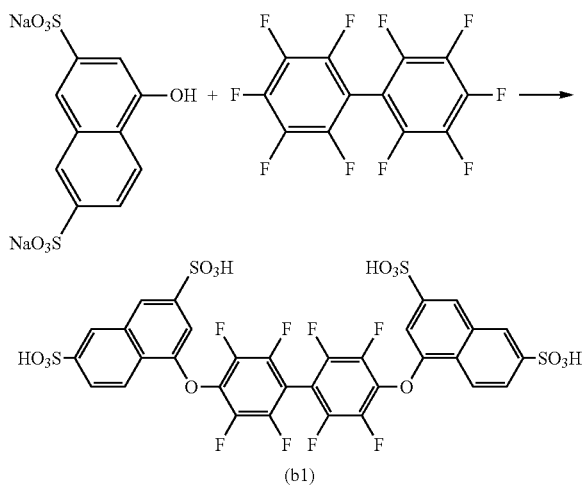

(b1)

That is, 4.797 g (14.36 mol) of perfluorobiphenyl, 4.167 g (30.15 mol) of potassium carbonate and 100 mL of N,N-dimethylformamide were successively added to 11 g (31.59 mmol) of thoroughly dried sodium 1-naphthol-3,6-disulfonate and the reaction system was flushed with nitrogen, following which the mixture was stirred for six hours at an internal temperature of 100° C.

The system was allowed to cool to room temperature, then an additional 500 mL of N,N-dimethylformamide was added and 90 minutes of stirring was carried out at room temperature in order to re-dissolve the Arylsulfonic Acid Compound 1 that precipitated out following the reaction. After stirring at room temperature, the solution was filtered to remove potassium carbonate residue and concentrated under reduced pressure. In addition, 100 mL of methanol was added to the residue in order to remove remaining impurities, and stirring was carried out at room temperature.

After 30 minutes of stirring at room temperature, the suspension was filtered, giving a residue. The residue was then dissolved by adding 300 mL of ultrapure water, and the resulting solution was ion-exchanged by column chromatography using Dowex 650C cation-exchange resin (from Dow Chemical; about 200 mL of H-type; distillation solvent: ultrapure water).

The fraction at or below pH 1 was concentrated to dryness in vacuo and the residue was dried to hardness in vacuo, giving 11 g of a yellow powder (yield, 85%).

[Example 1-1] Synthesis of Aniline Derivative 1

Aniline Derivative 1 (formula (a1) was synthesized by the following method.

[Chemical Formula 18]

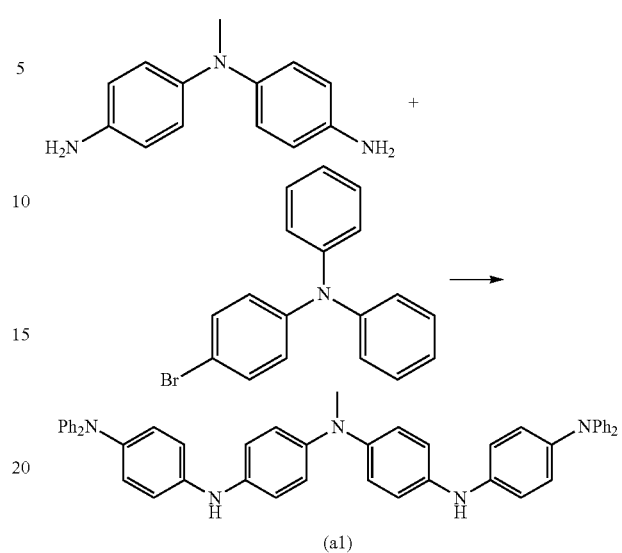

(a1)

A flask was charged with 5.02 g of N-methylbis(4-aminophenyl)amine, 16.03 g (2.1 eq.) of bromotriphenylamine, 0.11 g (0.5 mol %) of Pd$_2$(dba)$_3$, 0.24 g (5.0 mol %) of P(t-Bu)$_3$, 4.75 g (2.1 eq.) of sodium tert-butoxide (t-BuONa) and 50 g of toluene and flushed with nitrogen, then stirred for 3 hours under refluxing conditions.

The reaction solution was cooled to room temperature, after which ion-exchanged water and ethyl acetate were added and liquid-liquid extraction was carried out. The resulting organic phase was dried over magnesium sulfate.

Next, the solvent was driven off under reduced pressure and the residue was dissolved in a 1:4 (v/v) mixed solvent of dioxane and isopropanol. Reprecipitation was carried out by adding the resulting solution dropwise to methanol.

The precipitate collected by filtration was washed with ethyl acetate and thoroughly dried by heating in vacuo, giving 12 g of Aniline Derivative 1 (yield, 73%). The $^1$H-NMR results were as follows.

$^1$H-NMR (300 MHz, DMSO-d6) δ[ppm]: 7.94 (s, 2H), 7.21-7.25 (t, 8H), 6.86-7.02 (m, 28H), 3.17 (s, 3H).

[Example 1-2] Synthesis of Aniline Derivative 2

(1) N,N-Diphenyl-p-phenylenediamine (Formula (13)) was Synthesized as Follows

[Chemical Formula 19]

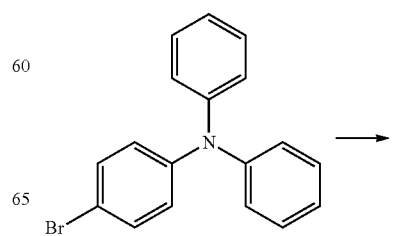

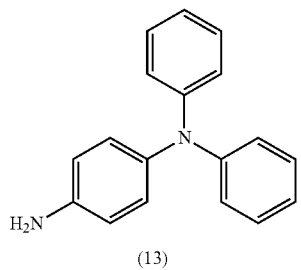

(13)

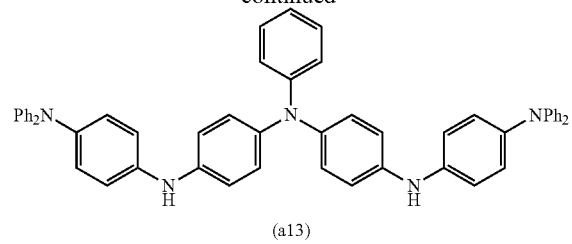

(a13)

A flask was charged with 4.04 g of bromotriphenylamine and 0.358 g (5 mol %) of Pd(dba)$_2$, and flushed with nitrogen. To this were successively added 40 mL of toluene, 5.24 mL of a toluene solution of P(t-Bu)$_3$ (24.02 g/L, 5 mol %), and 17.1 mL (1.09 M, 1.5 eq.) of lithium hexamethyldisilazide (LHMDS), followed by 4 hours of stirring at room temperature. A suitable amount of trifluoroacetic acid was then added and the system was stirred overnight.

After stirring was complete, liquid-liquid extraction was carried out using 30 mL of 2 mol/L aqueous sodium hydroxide, and the resulting organic phase was washed twice with ion-exchanged water. After washing, the organic phase was dried over sodium sulfate, then 0.4 g of activated carbon was added to the dried organic phase and the system was stirred at room temperature for 40 minutes. Next, the activated carbon was removed and the organic solvent was driven off under reduced pressure.

Recrystallization from the resulting residue was carried out using 4.3 g of toluene and 12.9 g of hexane, and the precipitate collected by filtration was thoroughly dried, giving 2.41 g of N,N-diphenyl-p-phenylenediamine (yield, 74%).

(2) Aniline Derivative 2 (Formula (a13)) was Synthesized as Follows

A flask was charged with 1.35 g of N,N-bis(p-bromophenyl)aniline, 1.91 g (2.2 eq.) of N,N-diphenyl-p-phenylenediamine, 0.193 g (5 mol %) of Pd(PPh$_3$)$_4$, 0.713 g (2.2 eq.) of t-BuONa and 20 mL of xylene and flushed with nitrogen, then stirred for 3.5 hours under refluxing conditions. After stirring was complete, the reaction mixture was allowed to cool to room temperature, then ion-exchanged water and chloroform were added and liquid-liquid extraction was carried out.

Next, the resulting organic phase was dried over sodium sulfate, following which the solvent was driven off under reduced pressure and the resulting residue was completely dissolved in 1,4-dioxane (12.5 g) heated to 80° C. To this was added 0.14 g of activated carbon and the system was stirred for 30 minutes. After stirring was complete, the activated carbon was removed by filtration while hot and the organic solvent was driven off under reduced pressure from the resulting filtrate. After dissolving the residue in 25 g of toluene, column chromatography was carried out and the fractions confirmed by a technique such as thin-layer chromatography (TLC) to contain the target substance were collected.

The solvent was driven off under reduced pressure from the collected fractions, following which the residue was dissolved in toluene (15.3 g) heated to 90° C. This solution was cooled to 0° C. and the precipitate collected by filtration was thoroughly dried, giving 1.14 g of Aniline Derivative 2 (yield, 45%). The $^1$H-NMR and MALDI-TOF-MS results were as follows.

$^1$H-NMR (300 MHz, DMSO-d6) δ[ppm]: 8.09 (s, 2H), 7.21-7.26 (m, 11H), 6.91-7.04 (m, 30H).

MALDI-TOF-MS, m/Z; found: 761.72 ([M]$^+$ calculated: 761.35)

[Example 1-3] Synthesis of Aniline Derivative 3

Aniline Derivative 3 (formula (a24)) was synthesized as follows.

[Chemical Formula 21]

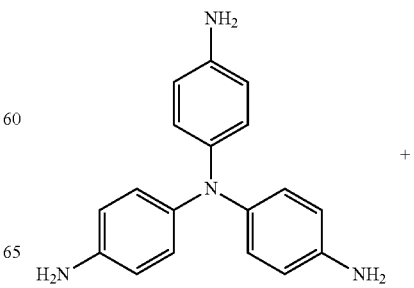

[Chemical Formula 20]

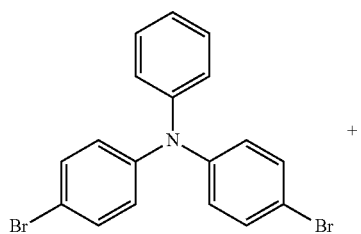

+

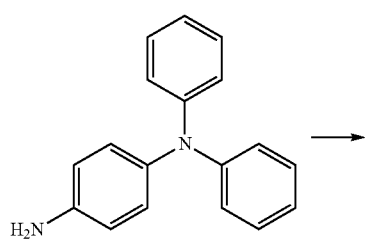

→

-continued

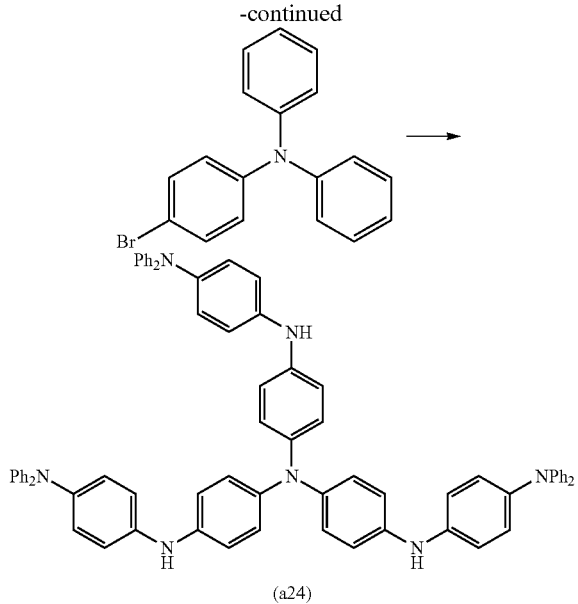

(a24)

A flask was charged with 1.46 g of tris(4-aminophenyl)amine, 5.35 g (3.3 eq.) of bromotriphenylamine, 0.299 g (5 mol %) of Pd(PPh$_3$)$_4$, 1.59 g (3.3 eq.) of t-BuONa and 50 mL of xylene and flushed with nitrogen, then stirred for 8 hours under refluxing conditions. After stirring was complete, the reaction mixture was allowed to cool to room temperature and 50 mL of chloroform was added, following which Celite filtration was carried out.

Liquid-liquid extraction was then carried out using this filtrate and saturated saline. The resulting organic phase was dried over sodium sulfate, following which the solvent was driven off under reduced pressure and short-column chromatography was carried out using the resulting residue and chloroform.

Activated carbon (0.5 g) was added to the resulting solution and the system was stirred for 30 minutes, following which the activated carbon was removed by filtration. The residue obtained by driving off the solvent from this filtrate was dissolved in a 1:1 (v/v) mixed solvent of chloroform and n-hexane.

Column chromatography was carried out on the resulting solution, the fractions confirmed by a technique such as TLC to contain the target substance were collected, and the solvent was driven off under reduced pressure.

The residue was dissolved in toluene and reprecipitation was carried out by adding n-hexane to the solution. The precipitate was collected by filtration and thoroughly dried under reduced pressure, giving 2.01 g of Aniline Derivative 3 (yield, 39%). The MALDI-TOF-MS results were as follows. MALDI-TOF-MS, m/Z; found: 1019.98 ([M]$^+$ calculated: 1019.47)

Example 2-1

A charge-transporting varnish was prepared by dissolving 0.062 g of Aniline Derivative 1 and 0.309 g of phosphotungstic acid (PTA) in 4 g of 1,3-dimethyl-2-imidazolidinone (DMI) within a nitrogen atmosphere, adding 6 g of cyclohexanol (CHA) and 2 g of propylene glycol (PG) to the resulting solution and stirring.

Example 2-2

Aside from changing the amounts of Aniline Derivative 1 and PTA to, respectively, 0.053 g and 0.318 g, a charge-transporting varnish was prepared in the same way as in Example 2-1.

Example 2-3

A charge-transporting varnish was prepared by dissolving 0.062 g of Aniline Derivative 2 and 0.309 g of PTA in 4 g of DMI within a nitrogen atmosphere, adding 6 g of CHA and 2 g of PG to the resulting solution and stirring.

Example 2-4

Aside from changing the amounts of Aniline Derivative 2 and PTA to, respectively, 0.053 g and 0.318 g, a charge-transporting varnish was prepared in the same way as in Example 2-3.

Example 2-5

A charge-transporting varnish was prepared by dissolving 0.062 g of Aniline Derivative 3 and 0.309 g of PTA in 4 g of DMI within a nitrogen atmosphere, adding 6 g of CHA and 2 g of PG to the resulting solution and stirring.

Example 2-6

Aside from changing the amounts of Aniline Derivative 3 and PTA to, respectively, 0.053 g and 0.318 g, a charge-transporting varnish was prepared in the same way as in Example 2-5.

Example 3-1

A charge-transporting varnish was prepared by dissolving 0.083 g of Aniline Derivative 1 and 0.161 g of Arylsulfonic Acid Compound 1 in 4 g of DMI within a nitrogen atmosphere, adding 6 g of CHA and 2 g of PG to the resulting solution and stirring.

Example 3-2

A charge-transporting varnish was prepared by dissolving 0.088 g of Aniline Derivative 2 and 0.157 g of Arylsulfonic Acid Compound 1 in 4 g of DMI within a nitrogen atmosphere, adding 6 g of CHA and 2 g of PG to the resulting solution and stirring.

Example 3-3

Aside from changing the amounts of Aniline Derivative 2 and Arylsulfonic Acid Compound 1 to, respectively, 0.073 g and 0.172 g, a charge-transporting varnish was prepared in the same way as in Example 3-2.

Example 3-4

A charge-transporting varnish was prepared by dissolving 0.082 g of Aniline Derivative 3 and 0.163 g of Arylsulfonic Acid Compound 1 in 4 g of DMI within a nitrogen atmosphere, adding 6 g of CHA and 2 g of PG to the resulting solution and stirring.

Example 3-5

Aside from changing the amounts of Aniline Derivative 3 and Arylsulfonic Acid Compound 1 to, respectively, 0.067 g and 0.178 g, a charge-transporting varnish was prepared in the same way as in Example 3-4.

Example 4-1

A charge-transporting varnish was prepared by dissolving 0.107 g of Aniline Derivative 1 and 0.138 g of Arylsulfonic Acid Compound 1 in 4 g of DMI within a nitrogen atmosphere, adding 6 g of CHA and 2 g of PG to the resulting solution and stirring, then adding 0.016 g of 3,3,3-trifluoropropyltrimethoxysilane and 0.008 g of phenyltrimethoxysilane and additionally stirring.

Example 4-2

Aside from changing the amounts of Aniline Derivative 1 and Arylsulfonic Acid Compound 1 to, respectively, 0.083 g and 0.161 g, a charge-transporting varnish was prepared in the same way as in Example 4-1.

Example 4-3

A charge-transporting varnish was prepared by dissolving 0.112 g of Aniline Derivative 2 and 0.133 g of Arylsulfonic Acid Compound 1 in 4 g of DMI within a nitrogen atmosphere, adding 6 g of CHA and 2 g of PG to the resulting solution and stirring, then adding 0.016 g of 3,3,3-trifluoropropyltrimethoxysilane and 0.008 g of phenyltrimethoxysilane and additionally stirring.

Examples 4-4 and 4-5

Aside from changing the amounts of Aniline Derivative 2 and Arylsulfonic Acid Compound 1 to, respectively, 0.088 g and 0.157 g (Example 4-4), and to, respectively, 0.073 g and 0.172 g (Example 4-5), charge-transporting varnishes were prepared in the same way as in Example 4-3.

Example 4-6

A charge-transporting varnish was prepared by dissolving 0.105 g of Aniline Derivative 3 and 0.140 g of Arylsulfonic Acid Compound 1 in 4 g of DMI within a nitrogen atmosphere, adding 6 g of CHA and 2 g of PG to the resulting solution and stirring, then adding 0.016 g of 3,3,3-trifluoropropyltrimethoxysilane and 0.008 g of phenyltrimethoxysilane and additionally stirring.

Examples 4-7 and 4-8

Aside from changing the amounts of Aniline Derivative 3 and Arylsulfonic Acid Compound 1 to, respectively, 0.082 g and 0.163 g (Example 4-7), or to, respectively, 0.067 g and 0.178 g (Example 4-8), charge-transporting varnishes were prepared in the same way as in Example 4-6.

Example 5

The varnishes obtained in Examples 2-1 to 4-8 were each coated onto ITO substrates using a spin coater, then dried at 50° C. for 5 minutes and baked in an open-air atmosphere at 230° C. for 15 minutes, thereby forming uniform 30 nm thin-films on the ITO substrates. Glass substrates with dimensions of 25 mm×25 mm×0.7 mm (t) and having indium-tin oxide (ITO) patterned on the surface to a film thickness of 150 nm were used as the ITO substrates. Prior to use, impurities on the surface were removed with an $O_2$ plasma cleaning system (150 W, 30 seconds).

Next, using a vapor deposition system (degree of vacuum, $1.0 \times 10^{-5}$ Pa), thin-films of N,N'-di(1-naphthyl)-N,N'-diphenylbenzidine (α-NPD), tris(8-quinolinolate) aluminum(III) ($Alq_3$), lithium fluoride and aluminum were successively deposited on the ITO substrates on which a thin-film had been formed, thereby giving organic EL devices. Vapor deposition was carried out at a rate of 0.2 nm/s for α-NPD, $Alq_3$ and aluminum, and at a rate of 0.02 nm/s for lithium fluoride. The film thicknesses were set to, respectively, 30 nm, 40 nm, 0.5 nm and 120 nm.

To prevent the device characteristics from deteriorating due to the influence of oxygen, moisture and the like in air, the organic EL devices were sealed with sealing substrates, after which the characteristics were evaluated. Sealing was carried out as follows.

The organic EL device was placed between sealing substrates in a nitrogen atmosphere having an oxygen concentration of not more than 2 ppm and a dew point of −85° C. or below, and the sealing substrates were laminated together using an adhesive (XNR5516Z-B1, from Nagase ChemteX Corporation). A desiccant (HD-071010W-40, from Dynic Corporation) was placed, together with the organic EL device, within the sealing substrates at this time.

The adhesive was cured by irradiating the laminated sealing substrates with UV light (wavelength, 365 nm; dosage, 6,000 mJ/cm$^2$), then annealing at 80° C. for 1 hour.

The current densities and brightnesses of these devices were measured at a driving voltage of 5 V.

The results for the devices produced using the varnishes of Examples 2-1 to 2-6 are shown in Table 1, the results for the devices produced using the varnishes of Examples 3-1 to 3-6 are shown in Table 2, and the results for the devices produced using the varnishes of Examples 4-1 to 4-8 are shown in Table 3.

TABLE 1

|  | Current density (mA/cm$^2$) | Brightness (cd/m$^2$) | Current efficiency (cd/A) |
|---|---|---|---|
| Example 2-1 | 89 | 2,419 | 2.7 |
| Example 2-2 | 126 | 3,241 | 2.6 |
| Example 2-3 | 65 | 1,959 | 3.0 |
| Example 2-4 | 95 | 2,727 | 2.9 |
| Example 2-5 | 87 | 2,442 | 2.8 |
| Example 2-6 | 108 | 3,058 | 2.8 |

TABLE 2

|  | Current density (mA/cm$^2$) | Brightness (cd/m$^2$) | Current efficiency (cd/A) |
|---|---|---|---|
| Example 3-1 | 62 | 1,829 | 2.9 |
| Example 3-2 | 69 | 2,091 | 3.0 |
| Example 3-3 | 78 | 2,296 | 3.0 |
| Example 3-4 | 88 | 2,596 | 3.0 |
| Example 3-5 | 88 | 2,567 | 2.9 |

TABLE 3

|  | Current density (mA/cm$^2$) | Brightness (cd/m$^2$) | Current efficiency (cd/A) |
| --- | --- | --- | --- |
| Example 4-1 | 82 | 2,288 | 2.8 |
| Example 4-2 | 77 | 2,205 | 2.9 |
| Example 4-3 | 64 | 2,063 | 3.2 |
| Example 4-4 | 70 | 2,132 | 3.0 |
| Example 4-5 | 94 | 2,779 | 3.0 |
| Example 4-6 | 107 | 3,173 | 3.0 |
| Example 4-7 | 108 | 3,154 | 2.9 |
| Example 4-8 | 111 | 3,194 | 2.9 |

As shown in Table 1, by using charge-transporting varnishes containing an aniline derivative of the invention and phosphotungstic acid, it was possible to produce charge-transporting thin-films suitable as hole injection layers that enable EL devices having excellent electrical characteristics to be achieved.

Likewise, as shown in Table 2, by using charge-transporting varnishes containing an aniline derivative of the invention and an arylsulfonic acid compound, it was possible to produce charge-transporting thin-films suitable as hole injection layers that enable EL devices having excellent electrical characteristics to be achieved.

Moreover, as shown in Table 3, by using charge-transporting varnishes containing an aniline derivative of the invention, an arylsulfonic acid compound and an organosilane compound, it was possible to produce charge-transporting thin-films suitable as hole injection layers that enable EL devices having excellent electrical characteristics to be achieved.

Durability tests were carried out on the devices fabricated using the varnishes from Examples 2-5, 2-6, 3-1 to 3-5 and 4-1 to 4-8. Table 4 shows the brightness half-lives (initial brightness, 5,000 cd/m$^2$).

TABLE 4

|  | Half-life (hours) |
| --- | --- |
| Example 2-5 | 313 |
| Example 2-6 | 305 |
| Example 3-1 | 358 |
| Example 3-2 | 355 |
| Example 3-3 | 256 |
| Example 3-4 | 447 |
| Example 3-5 | 381 |
| Example 4-1 | 334 |
| Example 4-2 | 255 |
| Example 4-3 | 449 |
| Example 4-4 | 356 |
| Example 4-5 | 335 |
| Example 4-6 | 475 |
| Example 4-7 | 428 |
| Example 4-8 | 431 |

As shown in Table 4, organic EL devices provided with charge-transporting thin-films obtained from charge-transporting varnishes of the invention had excellent durabilities.

The invention claimed is:

1. An aniline derivative characterized by having formula (1)

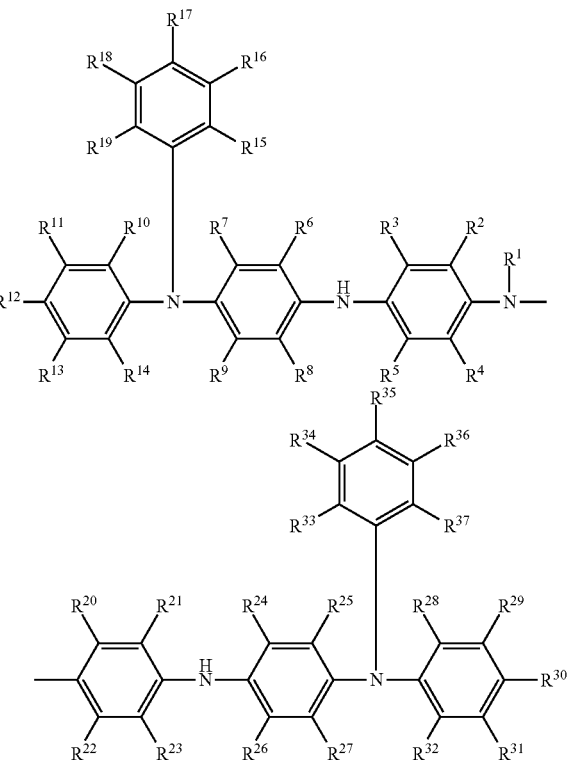

wherein $R^1$ is a group of formula (2)

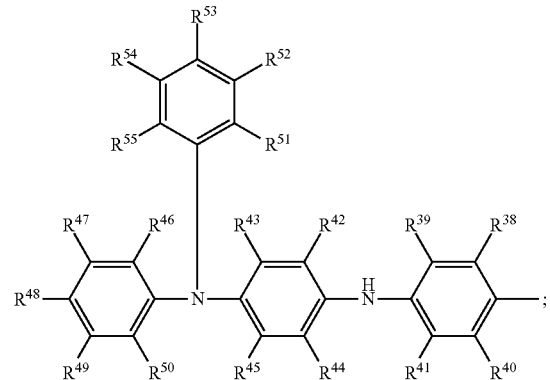

wherein $R^2$ to $R^{55}$ are each independently a hydrogen atom, a halogen atom, a nitro group, a cyano group, an aldehyde group, a hydroxyl group, a thiol group, a carboxyl group, an optionally substituted alkyl group of 1 to 20 carbon atoms, wherein the optional substitution is one or more of $Z^1$, an optionally substituted alkenyl group of 2 to 20 carbon atoms, wherein the optional substitution is one or more of $Z^1$, an optionally substituted alkynyl group of 2 to 20 carbon atoms, wherein the optional substitution is one or more of $Z^1$, an optionally substituted aryl group of 6 to 20 carbon atoms, wherein the optional substitution is one or more of $Z^2$, an optionally substituted heteroaryl group of 2 to 20 carbon atoms, wherein the optional substitution is one or more of $Z^2$, —C(O)$Y^1$, —O$Y^2$, —S$Y^3$, —C(O)O$Y^4$, —OC(O)$Y^5$, —C(O)NH$Y^6$ or —C(O)N$Y^7Y^8$;
- wherein $Y^1$ to $Y^8$ are each independently an optionally substituted alkyl group of 1 to 20 carbon atoms, wherein the optional substitution is one or more of $Z^1$, an optionally substituted alkenyl group of 2 to 20 carbon atoms, wherein the optional substitution is one or more of $Z^1$, an optionally substituted alkynyl group of 2 to 20 carbon atoms, wherein the optional substitution is one or more of $Z^1$, an optionally substituted aryl group of 6 to 20 carbon atoms, wherein the optional substitution is one or more of $Z^2$, or an optionally substituted heteroaryl group of 2 to 20 carbon atoms, wherein the optional substitution is one or more of $Z^2$;
- wherein $Z^1$ is a halogen atom, a nitro group, a cyano group, an aldehyde group, a hydroxyl group, a thiol group, a sulfonic acid group, a carboxyl group, an optionally substituted aryl group of 6 to 20 carbon atoms, wherein the optional substitution is one or more of $Z^3$, or an optionally substituted heteroaryl group of 2 to 20 carbon atoms, wherein the optional substitution is one or more of $Z^3$;
- wherein $Z^2$ is a halogen atom, a nitro group, a cyano group, an aldehyde group, a hydroxyl group, a thiol group, a sulfonic acid group, a carboxyl group, an optionally substituted alkyl group of 1 to 20 carbon atoms, wherein the optional substitution is one or more of $Z^3$, an optionally substituted $Z^3$, or an optionally substituted alkynyl group of 2 to 20 carbon atoms, wherein the optional substitution is one or more of $Z^3$; and
- wherein $Z^3$ is a halogen atom, a nitro group, a cyano group, an aldehyde group, a hydroxyl group, a thiol group, a sulfonic acid group or a carboxyl group.

2. The aniline derivative of claim 1, wherein $R^2$ to $R^{37}$ are a hydrogen atom, a halogen atom, an optionally substituted alkyl group of 1 to 20 carbon atoms, wherein the optional substitution is one or more of $Z^1$, an optionally substituted aryl group of 6 to 20 carbon atoms, wherein the optional substitution is one or more of $Z^2$, or —O$Y^2$.

3. The aniline derivative of claim 1, wherein $R^{38}$ to $R^{55}$ are a hydrogen atom, a halogen atom, an optionally substituted alkyl group of 1 to 20 carbon atoms, wherein the optional substitution is one or more of $Z^1$, an optionally substituted aryl group of 6 to 20 carbon atoms, wherein the optional substitution is one or more of $Z^2$, or —O$Y^2$.

4. A charge-transporting substance consisting of the aniline derivative of claim 1.

5. A charge-transporting varnish comprising the aniline derivative of claim 1, a dopant and an organic solvent.

6. A charge-transporting thin-film produced using the charge-transporting varnish of claim 5.

7. A charge-transporting thin-film comprising the aniline derivative of claim 1.

8. An electronic device comprising at least one charge-transporting thin-film of claim 6 or 7.

9. An organic electroluminescent device comprising at least one charge-transporting thin-film of claim 6 or 7.

10. The organic electroluminescent device of claim 9, wherein the charge-transporting thin-film is a hole injection layer or a hole transport layer.

11. A method of preparing the aniline derivative of claim 1, comprising the step of reacting an amine compound of formula (3), an amine compound of formula (4) and an amine compound of formula (5) in the presence of a catalyst

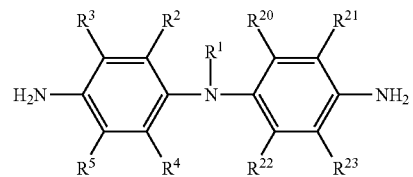

(3)

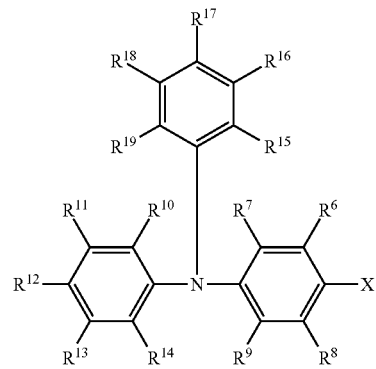

(4)

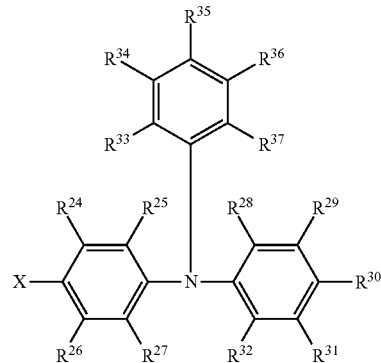

(5)

wherein $R^1$ to $R^{37}$ are as defined in claim 1, and X is a halogen atom or a pseudo-halogen group.

12. A method of preparing the aniline derivative of claim 1, comprising the step of reacting an amine compound of formula (6), an amine compound of formula (7) and an amine compound of formula (8) in the presence of a catalyst

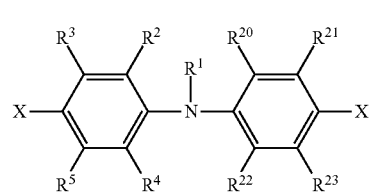

(6)

(7)

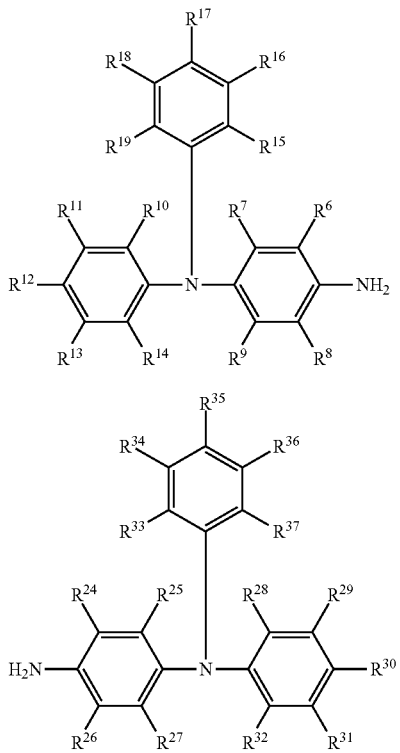

(8)

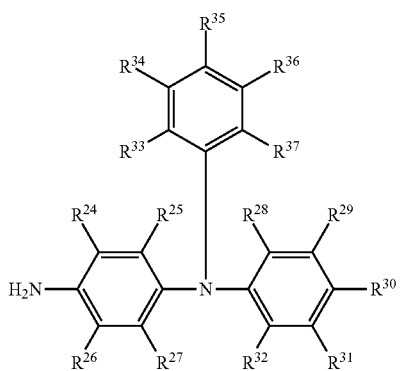

wherein $R^1$ to $R^{37}$ are as defined in claim 1, and X is a halogen atom or a pseudo-halogen group.

13. A method of preparing the aniline derivative of claim 1, comprising the step of reacting an amine compound of formula (9), an amine compound of formula (4), an amine compound of formula (5) and an amine compound of formula (10) in the presence of a catalyst (9)

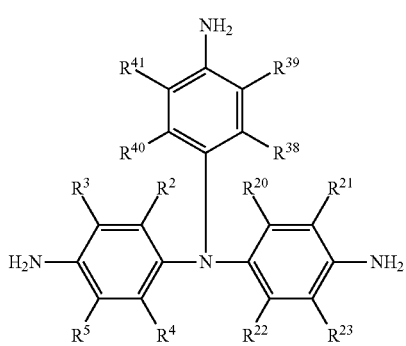

(4)

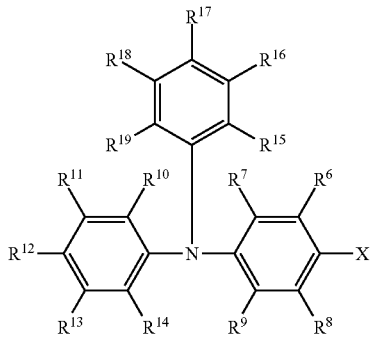

(5)

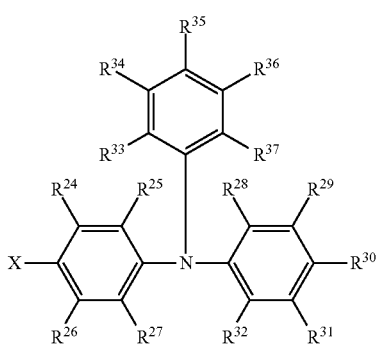

(10)

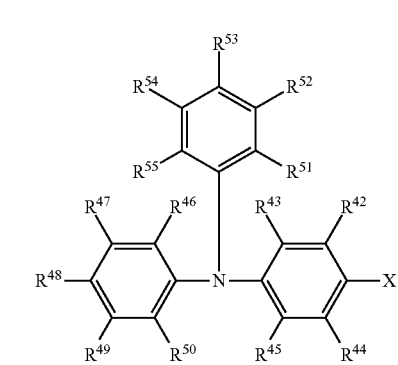

wherein $R^1$ to $R^{55}$ are as defined in claim 1, and X is a halogen atom or a pseudo-halogen group.

* * * * *